(12) United States Patent
Cortez, Jr.

(10) Patent No.: US 12,727,877 B2
(45) Date of Patent: Sep. 8, 2026

(54) SURGICAL SUTURE TENSIONING AND LABELING

(71) Applicant: Edwards Lifesciences Corporation, Irvine, CA (US)

(72) Inventor: Felino V. Cortez, Jr., Bowie, MD (US)

(73) Assignee: Edwards Lifesciences Corporation, Irvine, CA (US)

( * ) Notice: Subject to any disclaimer, the term of this patent is extended or adjusted under 35 U.S.C. 154(b) by 897 days.

(21) Appl. No.: 17/805,439

(22) Filed: Jun. 3, 2022

(65) Prior Publication Data

US 2022/0287708 A1 Sep. 15, 2022

Related U.S. Application Data

(63) Continuation of application No. PCT/US2020/062589, filed on Nov. 30, 2020.
(Continued)

(51) Int. Cl.
*A61B 17/04* (2006.01)
*A61B 90/92* (2016.01)
(Continued)

(52) U.S. Cl.
CPC .......... *A61B 17/0482* (2013.01); *A61B 90/92* (2016.02); *A61B 90/94* (2016.02);
(Continued)

(58) Field of Classification Search
CPC ............................ A61F 2/2454–12013; A61B 17/12009–12013; A61B 17/0469;
(Continued)

(56) References Cited

U.S. PATENT DOCUMENTS 2,590,498 A * 3/1952 Bomberger ............ A01G 22/20 73/862.42
3,131,957 A 5/1964 Musto
(Continued)

FOREIGN PATENT DOCUMENTS

EP 0791330 A3 11/1997
EP 3505077 A1 7/2019
(Continued)

OTHER PUBLICATIONS

Alfieri, 0. et al., "The double-orifice technique in mitral valve repair: a +A198:A225simple solution for complex problems," (2001) J. Thorac. Cardiovasc. Surg., 122(4):674-681.
(Continued)

*Primary Examiner* — Elizabeth Houston
*Assistant Examiner* — Jonathan A Hollm
(74) *Attorney, Agent, or Firm* — Chang and Hale LLP

(57) ABSTRACT

A method of managing suture deployment onto a target organ tissue involves applying a label to a first portion of a first suture extending externally from a target organ, the first suture having a second portion deployed onto the target organ tissue within the target organ. The method further involves attaching a suture tab to the first portion or another portion of the first suture extending externally from the target organ, and applying tension to the first suture, wherein applying tension to the first suture comprises coupling the first suture to a tension guide and determining whether the tension is within a target range.

12 Claims, 14 Drawing Sheets

Related U.S. Application Data

(60) Provisional application No. 62/944,967, filed on Dec. 6, 2019.

(51) Int. Cl.
*A61B 90/94* (2016.01)
*A61F 2/24* (2006.01)
*A61B 17/00* (2006.01)
*G09B 23/30* (2006.01)

(52) U.S. Cl.
CPC .. *A61F 2/2457* (2013.01); *A61B 2017/00243* (2013.01); *A61B 2017/00424* (2013.01); *A61B 2017/00862* (2013.01); *A61B 2017/0496* (2013.01); *G09B 23/30* (2013.01)

(58) Field of Classification Search
CPC ......... A61B 17/06166–06195; A61B 17/0483; A61B 2017/047–048; A61B 2017/06171–0619; A61B 2017/1142; B43K 8/00–24; B43K 1/00; B43K 1/006; B43K 1/02–04; B43K 1/12
See application file for complete search history.

(56) References Cited

U.S. PATENT DOCUMENTS 3,752,516 A 8/1973 Mumma
4,403,797 A 9/1983 Ragland
4,662,376 A 5/1987 Belanger
4,712,542 A * 12/1987 Daniel .................. A61F 2/0805 606/96
4,807,625 A 2/1989 Singleton
5,035,701 A * 7/1991 Kabbara ................ A61B 90/06 606/144
5,144,961 A 9/1992 Chen et al.
5,147,316 A 9/1992 Castillenti
5,312,423 A 5/1994 Rosenbluth et al.
5,391,176 A 2/1995 de la Torre
5,405,352 A 4/1995 Weston
5,454,821 A 10/1995 Harm et al.
5,472,446 A 12/1995 de la Torre
5,507,754 A 4/1996 Green et al.
5,527,323 A 6/1996 Jervis et al.
5,554,184 A 9/1996 Machiraju
5,626,614 A 5/1997 Hart
5,643,293 A 7/1997 Kogasaka et al.
5,681,331 A 10/1997 de la Torre et al.
5,713,897 A * 2/1998 Goble .................... A61B 90/06 606/88
5,716,368 A 2/1998 de la Torre et al.
5,727,569 A 3/1998 Benetti et al.
5,728,109 A 3/1998 Schulze et al.
5,746,752 A 5/1998 Burkhart
5,769,862 A 6/1998 Kammerer et al.
5,797,928 A 8/1998 Kogasaka
5,824,065 A 10/1998 Gross
5,931,868 A 8/1999 Gross
5,954,443 A * 9/1999 Bacon ...................... B43K 8/02 401/192
5,957,936 A 9/1999 Yoon et al.
5,971,447 A 10/1999 Steck
6,010,531 A 1/2000 Donlon et al.
6,074,417 A 6/2000 Peredo
6,269,819 B1 8/2001 Oz et al.
6,332,893 B1 12/2001 Mortier et al.
6,562,051 B1 5/2003 Bolduc et al.
6,626,930 B1 9/2003 Allen et al.
6,629,534 B1 10/2003 St. Goar et al.
6,752,810 B1 6/2004 Gao et al.
6,840,246 B2 1/2005 Downing
6,921,408 B2 7/2005 Sauer
6,940,246 B2 9/2005 Mochizuki et al.
6,978,176 B2 12/2005 Lattouf
6,991,635 B2 1/2006 Takamoto et al.
6,997,950 B2 2/2006 Chawla
7,112,207 B2 9/2006 Allen et al.
7,291,168 B2 11/2007 Macoviak et al.
7,294,148 B2 11/2007 McCarthy
7,309,086 B2 12/2007 Carrier
7,316,706 B2 1/2008 Bloom et al.
7,373,207 B2 5/2008 Lattouf
7,431,692 B2 10/2008 Zollinger et al.
7,513,908 B2 4/2009 Lattouf
7,534,260 B2 5/2009 Lattouf
7,608,091 B2 10/2009 Goldfarb et al.
7,618,449 B2 11/2009 Tremulis et al.
7,632,308 B2 12/2009 Loulmet
7,635,386 B1 12/2009 Gammie
7,666,196 B1 2/2010 Miles
7,744,609 B2 6/2010 Allen et al.
7,823,466 B2 * 11/2010 Glass ...................... G01L 5/103 73/826
7,837,727 B2 11/2010 Goetz et al.
7,871,368 B2 1/2011 Zollinger et al.
7,871,433 B2 1/2011 Lattouf
7,959,650 B2 6/2011 Kaiser et al.
8,029,518 B2 10/2011 Goldfarb et al.
8,029,565 B2 10/2011 Lattouf
8,043,368 B2 10/2011 Crabtree
8,147,542 B2 4/2012 Maisano et al.
8,187,323 B2 5/2012 Mortier et al.
8,226,711 B2 7/2012 Mortier et al.
8,241,304 B2 8/2012 Bachman
8,252,050 B2 8/2012 Maisano et al.
8,292,884 B2 10/2012 Levine et al.
8,303,622 B2 11/2012 Alkhatib
8,317,806 B2 * 11/2012 Coe .................... A61B 17/0487 606/148
8,333,788 B2 12/2012 Maiorino
8,382,829 B1 2/2013 Call et al.
8,439,969 B2 5/2013 Gillinov et al.
8,454,656 B2 6/2013 Tuval
8,465,500 B2 6/2013 Speziali
8,475,525 B2 7/2013 Maisano et al.
8,500,800 B2 8/2013 Maisano et al.
8,608,758 B2 12/2013 Singhatat et al.
8,663,278 B2 3/2014 Mabuchi et al.
8,771,296 B2 7/2014 Nobles et al.
8,828,053 B2 9/2014 Sengun et al.
8,852,213 B2 10/2014 Gammie et al.
8,888,791 B2 11/2014 Jaramillo et al.
8,940,008 B2 1/2015 Kunis
9,131,884 B2 9/2015 Holmes et al.
9,192,287 B2 11/2015 Saadat et al.
2002/0013571 A1 1/2002 Goldfarb et al.
2003/0023254 A1 1/2003 Chiu
2003/0094180 A1 5/2003 Benetti
2003/0105519 A1 6/2003 Fasol et al.
2003/0120264 A1 6/2003 Lattouf
2003/0120341 A1 6/2003 Shennib et al.
2004/0044365 A1 3/2004 Bachman
2004/0093023 A1 5/2004 Allen et al.
2004/0199183 A1 10/2004 Oz et al.
2005/0004667 A1 1/2005 Swinford et al.
2005/0019735 A1 1/2005 Demas
2005/0075654 A1 4/2005 Kelleher
2005/0119735 A1 6/2005 Spence et al.
2005/0149067 A1 7/2005 Takemoto et al.
2005/0149093 A1 7/2005 Pokorney
2005/0154402 A1 7/2005 Sauer et al.
2005/0216036 A1 9/2005 Nakao
2005/0216077 A1 9/2005 Mathis et al.
2005/0261710 A1 11/2005 Sakamoto et al.
2005/0267493 A1 12/2005 Schreck et al.
2006/0030866 A1 2/2006 Schreck
2006/0100698 A1 5/2006 Lattouf
2006/0111739 A1 5/2006 Staufer et al.
2006/0167541 A1 7/2006 Lattouf
2006/0190030 A1 8/2006 To et al.
2006/0253126 A1 * 11/2006 Bjerken ............. A61B 17/0482 606/139
2006/0282088 A1 12/2006 Ryan

(56) References Cited

U.S. PATENT DOCUMENTS

| | | | | |
|---|---|---|---|---|
| 2007/0001857 | A1 | 1/2007 | Hartmann et al. | |
| 2007/0049952 | A1* | 3/2007 | Weiss | A61B 17/0218 606/144 |
| 2007/0055292 | A1 | 3/2007 | Ortiz et al. | |
| 2007/0112422 | A1 | 5/2007 | Dehdashtian | |
| 2007/0112425 | A1 | 5/2007 | Schaller et al. | |
| 2007/0118151 | A1 | 5/2007 | Davidson | |
| 2007/0118154 | A1 | 5/2007 | Crabtree | |
| 2007/0149995 | A1 | 6/2007 | Quinn et al. | |
| 2007/0197858 | A1 | 8/2007 | Goldfarb et al. | |
| 2007/0213582 | A1 | 9/2007 | Zollinger et al. | |
| 2007/0270793 | A1 | 11/2007 | Lattouf | |
| 2008/0004597 | A1 | 1/2008 | Lattouf et al. | |
| 2008/0009888 | A1 | 1/2008 | Ewers et al. | |
| 2008/0065203 | A1 | 3/2008 | Khalapyan | |
| 2008/0140093 | A1 | 6/2008 | Stone et al. | |
| 2008/0167714 | A1 | 7/2008 | St. Goar et al. | |
| 2008/0188893 | A1 | 8/2008 | Selvitelli et al. | |
| 2008/0195126 | A1 | 8/2008 | Solem | |
| 2008/0228223 | A1 | 9/2008 | Alkhatib | |
| 2008/0228266 | A1* | 9/2008 | McNamara | A61F 2/2445 623/2.36 |
| 2008/0249504 | A1 | 10/2008 | Lattouf et al. | |
| 2008/0269781 | A1 | 10/2008 | Funamura et al. | |
| 2009/0005863 | A1 | 1/2009 | Goetz et al. | |
| 2009/0043153 | A1 | 2/2009 | Zollinger et al. | |
| 2009/0105729 | A1 | 4/2009 | Zentgraf | |
| 2009/0105751 | A1 | 4/2009 | Zentgraf | |
| 2009/0276038 | A1 | 11/2009 | Tremulis et al. | |
| 2010/0023056 | A1 | 1/2010 | Johansson et al. | |
| 2010/0023117 | A1 | 1/2010 | Yoganathan et al. | |
| 2010/0023118 | A1 | 1/2010 | Medlock et al. | |
| 2010/0042147 | A1 | 2/2010 | Janovsky et al. | |
| 2010/0174297 | A1 | 7/2010 | Speziali | |
| 2010/0179574 | A1 | 7/2010 | Longoria et al. | |
| 2010/0210899 | A1 | 8/2010 | Schankereli | |
| 2010/0298930 | A1 | 11/2010 | Orlov | |
| 2011/0015476 | A1 | 1/2011 | Franco | |
| 2011/0022083 | A1 | 1/2011 | DiMatteo et al. | |
| 2011/0022084 | A1 | 1/2011 | Sengun et al. | |
| 2011/0028995 | A1 | 2/2011 | Miraki et al. | |
| 2011/0029071 | A1 | 2/2011 | Zlotnick et al. | |
| 2011/0060407 | A1 | 3/2011 | Ketai et al. | |
| 2011/0106106 | A1 | 5/2011 | Meier et al. | |
| 2011/0144743 | A1 | 6/2011 | Lattouf | |
| 2011/0264208 | A1 | 10/2011 | Duffy et al. | |
| 2011/0270278 | A1 | 11/2011 | Overes et al. | |
| 2011/0288637 | A1 | 11/2011 | De Marchena | |
| 2011/0307055 | A1 | 12/2011 | Goldfarb et al. | |
| 2012/0004669 | A1 | 1/2012 | Overes et al. | |
| 2012/0143215 | A1 | 6/2012 | Corrao et al. | |
| 2012/0150223 | A1 | 6/2012 | Manos et al. | |
| 2012/0179184 | A1 | 7/2012 | Orlov | |
| 2012/0184971 | A1 | 7/2012 | Zentgraf et al. | |
| 2012/0203072 | A1 | 8/2012 | Lattouf et al. | |
| 2012/0226294 | A1 | 9/2012 | Tuval | |
| 2012/0226349 | A1 | 9/2012 | Tuval et al. | |
| 2013/0018459 | A1 | 1/2013 | Maisano et al. | |
| 2013/0035757 | A1 | 2/2013 | Zentgraf et al. | |
| 2013/0253641 | A1 | 9/2013 | Lattouf | |
| 2013/0282059 | A1 | 10/2013 | Ketai et al. | |
| 2013/0345749 | A1 | 12/2013 | Sullivan et al. | |
| 2014/0031926 | A1 | 1/2014 | Kudlik et al. | |
| 2014/0039607 | A1 | 2/2014 | Kovach | |
| 2014/0067052 | A1 | 3/2014 | Chau et al. | |
| 2014/0114404 | A1 | 4/2014 | Gammie et al. | |
| 2014/0214152 | A1 | 7/2014 | Bielefeld | |
| 2014/0243968 | A1 | 8/2014 | Padala | |
| 2014/0364938 | A1 | 12/2014 | Longoria et al. | |
| 2015/0032127 | A1 | 1/2015 | Gammie et al. | |
| 2015/0045879 | A1 | 2/2015 | Longoria et al. | |
| 2018/0103947 | A1* | 4/2018 | Nobles | A61B 17/0483 |
| 2018/0185153 | A1* | 7/2018 | Bishop | A61F 2/2466 |
| 2019/0175346 | A1 | 6/2019 | Schaffner et al. | |
| 2020/0155315 | A1 | 5/2020 | Zhang et al. | |
| 2021/0137579 | A1* | 5/2021 | Rafiee | A61B 17/22 |

FOREIGN PATENT DOCUMENTS

| | | | |
|---|---|---|---|
| JP | 2013517110 | A | 5/2013 |
| WO | 2004037463 | A1 | 5/2004 |
| WO | 2006078694 | A3 | 7/2006 |
| WO | 2006127509 | A2 | 11/2006 |
| WO | 2007100268 | A2 | 9/2007 |
| WO | 2007119057 | A1 | 10/2007 |
| WO | 2008013869 | A2 | 1/2008 |
| WO | 2008124110 | A3 | 10/2008 |
| WO | 2008143740 | A3 | 11/2008 |
| WO | 2009081396 | A2 | 7/2009 |
| WO | 2010070649 | A1 | 6/2010 |
| WO | 2010105046 | A1 | 9/2010 |
| WO | 2012137208 | A1 | 10/2012 |
| WO | 2013003228 | A1 | 1/2013 |
| WO | 2014093861 | A1 | 6/2014 |
| WO | 2015020816 | A1 | 2/2015 |
| WO | 2016192481 | A1 | 12/2016 |

OTHER PUBLICATIONS

Barbero-Marcial, M. et al., "Transxiphoid Approach Without Median Sternotomy for the Repair of Atrial Septal Defects," (1998) Ann. Thorac. Surg., 65(3):771-774.

Braunberger, E. et al., "Very long-term results (more than 20 years) of valve repair with Carpentier's Techniques in nonrheumatic mitral valve insufficiency," (2001) Circulation, 104:I-8-I-11.

Carpentier, Alain, "Cardiac valve surgery—the 'French correction'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," ( 1991) J. Thorac. Cardiovasc. Surg., 101 (3):495-501.

David, T. E. et al., "Replacement of chordae tendineae with Gore-Tex sutures: a ten-year experience," (1996) J. Heart Valve Dis., 5(4):352-355.

Doty, D. B. et al., "Full-Spectrum Cardiac Surgery Through a Minimal Incision: Mini-Sternotomy (Lower Half) Technique," (1998) Ann. Thorac. Surg., 65(2):573-577.

Duran, C. M. G. et al., "Techniques for ensuring the correct length of new mitral chords," (2003) J Heart Valve Dis., 12(2):156-161.

Eishi, K. et al., "Long-term results of artificial chordae implantation in patients with mitral valve prolapse," (1997) J. Heart Valve Dis., 6(6):594-598.

Frater, R. W. M. et al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal of Cardio-thoracic Surgery, 29:380-385.

Hvass, U. et al., "Papillary Muscle Sling: A New Functional Approach to Mitral Repair in Patients With Ischernic Left Ventricular Dysfunction and Functional Mitral Regurgitation," (2003) Ann. Thorac. Surg., 75:809-811.

Kasegawa, H. et al., "Simple method for determining proper length of artificial chordae in mitral valve repair," (1994) Ann. Thorac. Surg., 57(1 ):237-239.

Kobayashi, J. et al., "Ten-year experience of chordal replacement with expanded polytetrafluoroethylene in mitral valve repair," (2000) Circulation, 102(19 Suppl 3):III-30-III-34.

Kunzelman, K. et al., "Replacement of mitral valve posterior chordae tendineae with expanded polytetrafluorocthylcnc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorac. Cardiovasc. Surg., 133( 1): 247-249.

Maisano, F. et al., "The double-orifice technique as a standardized approach to treat mitral regurgitation due to severe myxomatous

(56) References Cited

OTHER PUBLICATIONS disease: surgical technique," (2000) European Journal of Cardio-thoracic Surgery, 17(3):201-205.
Merendino, K. A. et al., "The open correction of rheumatic mitral regurgitation and/or stenosis with special reference to regurgitation treated by posterornedial annuloplasty utilizing a pump-oxygenator," (1959) Annals of Surgery, 150 (1 ):5-22.
Minatoya, K. et al., "Pathologic aspects of polytetrafluoroethylene sutures in human heart," ( 1996) Ann. Thorac. Surg., 61 (3 ):883-887.
Mohty, D. et al., "Very long-term survival and durability of mitral valve repair for mitral valve prolapse," (2001) Circulation, 104:I-1-I-7.
*Neochord, Inc.* v. *University of Maryland, Bal Tim Ore*, Case No. IPR2016-00208, Decision on Institution of Inter Parties Review,37 CFR §42. 108, Paper 6, Entered May 24, 2016, 28 pages.
*Neochord, Inc.* v. *University of Maryland, Baltimore*, Case No. IPR2016-00208, Declaration of Dr. Lishan Aklog, dated Nov. 17, 2015, 91 pages.
*Neochord, Inc.* v. *University of Maryland, Baltimore*, Case No. IPR2016-00208, Petition for inter ParlesReview of U.S. Pat. No. 7,635,386, dated Nov. 18, 2015, 65 pages.
Nigro, J. J. et al., "Neochordal repair of the posterior mitral leaflet," (2004) J. Thoraric. Cardiovasc. Surg., 127(2):440-447.
Phillips, M. R. et al., "Repair of anterior leaflet mitral valve prolapse: chordal replacement versus chordal shortening," (2000) Ann. Thorac. Surg., 69(1 ):25-29.
Russo, M. J et al. •Transapical Approach for Mitral Valve Repair during Insertion of a Left Ventricular Assist Device, Hindawi Publishing Corporation, The Scientific World Journal, vol. 2013, Article ID 925310, [online], Retrieved from the internet: <URL: http://dx.doi.org/J 0.1155/2013/92531 O> Apr. 11, 2013, 4 pages.
Sarsam, M.A. I., "Simplified technique for determining the length of artificial chordae in milral valve repair," (2002) Ann. Thorac. Surg., 73(5): 1659-1660.
Savage, E. B. et al., Use of mitral valve repair: analysis of contemporary United States experience reported to the society of thoracic surgeons national cardiac database, . . . (2003) Ann. Thorac. Surg., 75:820-825.
Speziali, G. et al., "Correction of Mitral Valve Regurgitation by Off-Pump, Transapical Placement of Artificial Chordae Tendinae, Results of the European TACT Trial," AATS 93rd Annual Meeting 2013, www.aats.org, 26 pages.
Suematsu, Y. et al., "Three-dimensional echo-guided beating heart surgery without cardiopulmonary bypass: Atrial septal defect closure in a swine model," (2005) J. Thorac. Cardiovasc. Surg., 130: 1348-1357.
Von Oppell, U. 0 et al., "Chordal replacement for both minimally invasive and conventional mitral valve surgery using premeasured Gore-Tex loops," (2000) Ann. Thorac. Surg., 70(6):2166-2168.
Zussa, C. et al., Artificial mitral valve chordae: experimental and clinical experience ;• (1990) Ann. Thorac. Surg., 50(3):367-373.
Zussa, C. et al., "Seven-year experience with chordal replacement with expanded polytetrafluoroethylene in floppy mitral valve," (1994) J. Thorac. Cardiovasc. Surg., 108(1):37-41.
Zussa, C. et al., "Surgical technique for artificial rnitral chordae implantation," (1991) Journal of Cardiac Surgery, 6(4):432-438.
Zussa, C., "Artificial chordae," (1995) J. Heart Valve Dis., 4(2):S249-S256.

* cited by examiner 200
222
204
202
224
210
216
208
214
212
206
220
218

SURGICAL SUTURE TENSIONING AND LABELING

CROSS REFERENCE TO RELATED APPLICATIONS

This application is a continuation of International Patent Application No. PCT/US2020/062589, filed Nov. 30, 2020, which claims the benefit of U.S. Application No. 62/944,967, filed on Dec. 6, 2019, the disclosures all of which are hereby incorporated by reference for all purposes.

BACKGROUND

Technical Field

This disclosure herein relates performing cardiac valve repairs, and more particularly, the disclosure relates to methods and devices for surgical suture tensioning and labeling used in performing minimally invasive mitral valve repairs through a minimally invasive incision, while the heart is beating.

Description of Related Art

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease), and infectious processes (e.g., endocarditis). Additionally, damage to the ventricle from prior heart attacks (e.g., myocardial infarction secondary to coronary artery disease) or other heart diseases (e.g., cardiomyopathy) can distort the geometry of the heart causing valves in the heart to dysfunction. The vast majority of patients undergoing valve surgery, such as mitral valve surgery, suffer from a degenerative disease that causes a malfunction in a leaflet of the valve, which results in prolapse and regurgitation.

Valve regurgitation occurs when the leaflets of the valve do not close completely thereby allowing blood to leak back into the prior chamber when the heart contracts. There are three mechanisms by which a valve becomes regurgitant or incompetent; they include Carpentier's type I, type II and type III malfunctions. A Carpentier type I malfunction involves the dilation of the annulus such that the area of the valve orifice increases. The otherwise normally functioning leaflets do not have enough surface area to cover the enlarged orifice and fail to form a tight seal (e.g., do not coapt properly) causing regurgitation. Included in a type I mechanism malfunction are perforations of the valve leaflets, as in endocarditis. A Carpentier's type II malfunction involves prolapse of a segment of one or both leaflets above the plane of coaptation. This is the most commonly treated cause of mitral regurgitation, and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic heart disease (IIIa) or dilation of the ventricle (IIIb).

Mitral valve disease is the most common valvular heart disorder, with nearly 4 million Americans estimated to have moderate to severe mitral valve regurgitation ("MR"), with similar numbers of individuals impacted outside of the United States. MR results in a volume overload on the left ventricle which in turn progresses to ventricular dilation, decreased ejection performance, pulmonary hypertension, symptomatic congestive heart failure, atrial fibrillation, right ventricular dysfunction and death. Successful surgical mitral valve repair restores mitral valve competence, abolishes the volume overload on the left ventricle, improves symptom status, and prevents adverse left ventricular remodeling. While generally safe and effective, conventional open-heart operations are invasive, result in significant disability, and require extended post-procedure recovery. Patients routinely spend five to seven days in the hospital and often are not able to return to normal daily activities for a month or more.

In many instances of mitral valve regurgitation, repair is preferable to valve replacement. There is a significant need to perform mitral valve repairs using less invasive procedures while the heart is still beating. Accordingly, there is a continuing need for new procedures and devices for performing cardiac valve repairs, such as mitral valve repair, which are less invasive, do not require cardiac arrest, and are less labor-intensive and technically challenging.

SUMMARY

Described herein are one or more methods and/or devices to facilitate desired tensioning and/or identification of individual sutures or pairs of sutures deployed onto a target organ tissue, such as a mitral valve leaflet.

In some implementations, the present disclosure relates to a method of managing suture deployment onto a target organ tissue. The method comprises coupling a first portion of a first suture to a tension guide, the first portion of the first suture extending externally from a target organ, the first suture having a second portion deployed onto the target organ tissue within the target organ. The method further comprises applying tension to the first suture, wherein applying tension to the first suture comprises applying a force upon the tension guide coupled to the first suture and determining whether the tension is within a target range using the tension guide.

The method may further comprises applying a label to the first portion or another portion of the first suture extending externally from the target organ. For example, applying the label can comprise coloring the first portion or the other portion of the first suture. In some examples, coloring comprises running the first portion or the other portion of the first suture through a groove of a coloring applicator tip portion.

The method may further comprise coupling a suture tab to the first portion or another portion of the first suture extending externally from the target organ. For example, coupling the suture tab can comprise winding the first portion or the other portion of the first suture around a pair of notches on the suture tab. Furthermore, coupling the first portion of the first suture to the tension guide can comprise engaging the tension guide with the suture tab.

In some examples, coupling the first portion of the first suture to the tension guide comprises engaging the tension guide with the first suture. The tension guide can comprise an elastic mechanical energy storage, and wherein applying the tension to the first suture comprises applying a force upon the tension guide coupled to the first suture to cause deformation of the elastic mechanical energy storage. For example, determining whether the tension is within a target range can comprise determining whether deformation of the elastic mechanical energy storage is within a target deformation range. In some examples, the elastic mechanical energy storage comprises a mechanical spring, and wherein determining whether deformation of the elastic mechanical energy storage is within a target deformation range comprises observing whether compression of the spring is less than a threshold compression.

The method may further comprise deploying a second suture onto a second site of the target organ tissue, selection of the second site being based at least in part on a response of the target organ tissue to the tension applied to the first suture. In some examples, the target organ is the heart. The target organ tissue may be a mitral valve leaflet.

In some implementations, the present disclosure relates to a method of managing suture deployment onto a target organ tissue. The method comprises applying a label to a first portion of a first suture, the first portion of the first suture extending externally from a target organ, the first suture having a second portion deployed onto the target organ tissue within the target organ. The method further comprises coupling a suture tab to the first portion or another portion of the first suture extending externally from the target organ.

Applying the label can comprise coloring the first portion of the first suture. For example, coloring can comprise running the first portion of the first suture through a groove of a coloring applicator tip portion. In some examples, coupling the suture tab comprises winding the first portion or the other portion of the first suture around a pair of notches on the suture tab.

In some examples, the method further comprises applying tension to the first suture, wherein applying tension to the first suture comprises engaging the suture tab and applying a force upon the suture tab. For example, the method may further comprise deploying a second suture onto a second site of the target organ tissue, selection of the second site being based at least in part on a response of the target organ tissue to the tension applied to the first suture. In some examples, the target organ is the heart. In some examples, the target organ tissue is a mitral valve leaflet.

In some implementations, the present disclosure relates to a kit for managing suture deployment onto a target organ tissue. The kit comprises a label applicator configured to apply a color to a portion of a suture, a suture tab configured to be coupled to the suture, and a tension guide, the tension guide comprising an engagement portion configured to couple to the suture, an elastic mechanical energy storage configured to deform in response to tension applied to the engagement portion, and an indicator configured to indicate whether deformation of the elastic mechanical energy storage is within a target range.

The label applicator can comprise a coloring marker. In some examples, the label applicator comprises an applicator tip portion comprising a groove configured to receive the suture. The suture tab can comprise a pair of notches to receive the suture and couple to the suture. In some examples, the elastic mechanical energy storage comprises a mechanical spring. For example, the indicator may comprise a plurality of visual markers on an exterior of a housing of the tension guide indicative of whether a degree of compression of the mechanical spring is within the target range. In some examples, the target organ tissue is a mitral valve leaflet.

Methods disclosed herein also encompass simulations of the method, for example, for teaching, demonstration, or method developments. Such simulations may be performed on a simulated patient or portion thereof—for example, an anthropomorphic ghost—which can be a physical simulation, a virtual simulation, or any combination thereof. Physical simulations can include manufactured or cadaver models, which can be human or animal. Virtual simulations can include in silico models, projections, holograms, or the like. Simulations can also include tactile, audio, or other sensory elements.

For purposes of summarizing the disclosure, certain aspects, advantages and novel features have been described herein. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

These and other features, aspects, and advantages of the present disclosure are described with reference to the drawings of some examples, which are intended not to limit the invention but to illustrate the examples.

FIGS. 6A through 6E show an example of attaching a suture tab and application of a color label onto a pair of sutures.

DETAILED DESCRIPTION

The headings provided herein, if any, are for convenience only and do not necessarily affect the scope or meaning of the claimed invention.

Figure 1:
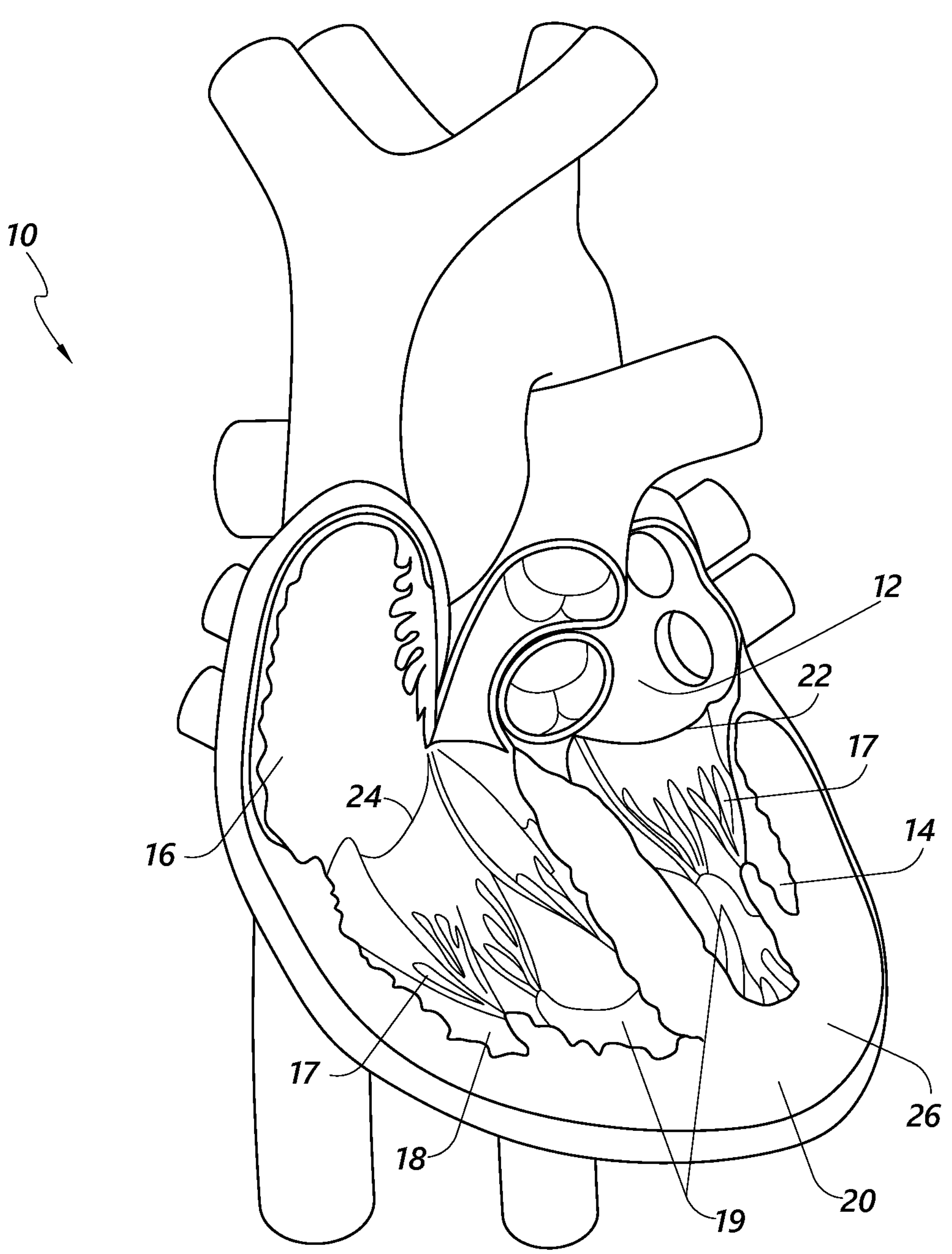
FIG. 1 is a cut-away anterior view of a heart.

FIG. 1 is a cut away view of a heart 10. The heart 10 has four chambers, the left atrium 12, left ventricle 14, right atrium 16, or right ventricle 18. The left atrioventricular valve, the mitral valve 22, controls the passage of oxygenated blood from the left atrium 12 to the left ventricle 14. Access into a chamber 12, 14, 16, 18 in the heart 10 may be made at any suitable site of entry but is preferably made in the apex region of the heart, for example, slightly above the apex 26 at the level of the papillary muscles 19. Typically, access into the left ventricle 14, for instance, to perform a mitral valve repair, is gained through a process performed in the apical region, close to (or slightly skewed toward the left of) the median axis of the heart 10. Generally, an apex region of the heart is a bottom region of the heart that is within the left or right ventricular region and is below the mitral valve 22 and tricuspid valve 24 and toward the tip or apex 26 of the heart 10. More specifically, an apex region (AR) of the heart is within a few centimeters to the right or to the left of the septum 20 of the heart 10 at or near the level of the papillary muscles 19. Accordingly, the ventricle can be accessed directly via the apex 26, or via an off apex location that is in the apical or apex region AR, but slightly removed from the apex 26, such as via a lateral ventricular wall, a region between the apex 26 and the base of a papillary muscle 19, or even directly at the base of a papillary muscle 19 or above. Typically, the incision made to access the appropriate ventricle of the heart is no longer than about, for example, about 0.5 cm. Alternatively, access can be obtained using the Seldinger technique.

Figure 2:
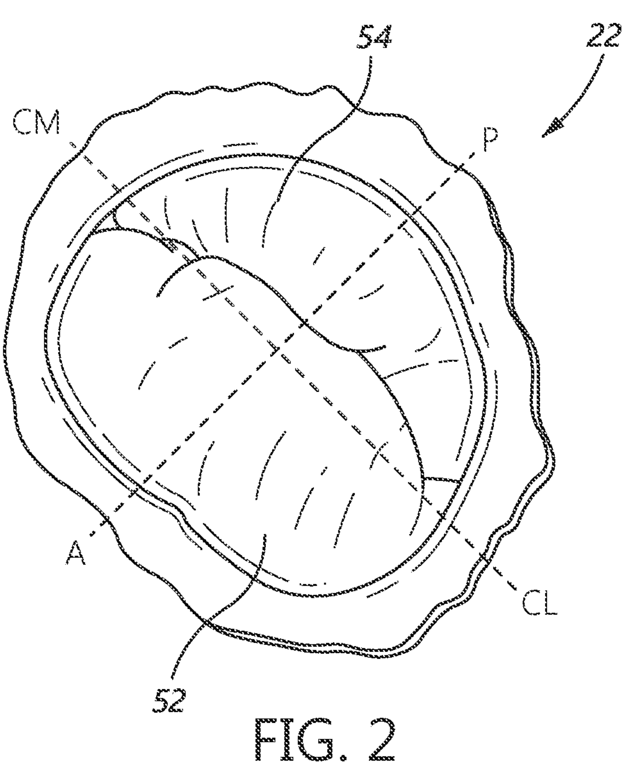
FIG. 2 is a top perspective view of a healthy mitral valve with the mitral leaflets closed.

FIG. 2 is a top perspective view of the mitral valve 22 with the mitral leaflets closed. The mitral valve 22 includes two leaflets, the anterior leaflet 52 and the posterior leaflet 54. Referring back to FIG. 1, the mitral valve 22 has two papillary muscles 19, the anteromedial and the posterolateral papillary muscles which attach the leaflets 52, 54 to the walls of the left ventricle 14 via the chordae tendineae 17.

Figure 3:
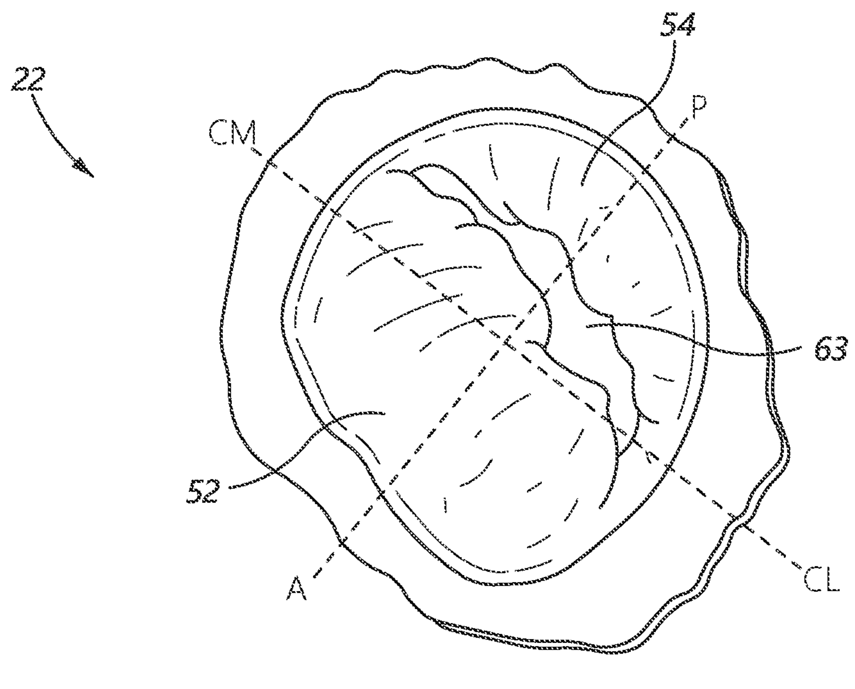
FIG. 3 is a top perspective view of a dysfunctional mitral valve with a visible gap between the mitral leaflets.

FIG. 3 is a top perspective view of the mitral valve 22 with a visible gap between the mitral leaflets. The mitral valve 22 shown in FIG. 3 is prolapsed. Prolapse occurs when a prolapsed segment of a leaflet 52, 54 of the mitral valve 22 is displaced above the plane of the mitral annulus into the left atrium 12 preventing the leaflets from properly sealing together to form the natural plane or line of coaptation between the valve leaflets during systole. Because one or more of the leaflets 52, 54 malfunctions, the mitral valve 22 does not close properly, and, therefore, the leaflets 52, 54 fail to coapt. This failure to coapt causes a gap 63 between the leaflets 52, 54 that allows blood to flow back into the left atrium, during systole, while it is being ejected by the left ventricle. As set forth above, there are several different ways a leaflet may malfunction, which can thereby lead to regurgitation.

Mitral valve regurgitation increases the workload on the heart and may lead to very serious conditions if left untreated, such as decreased ventricular function, pulmonary hypertension, congestive heart failure, permanent heart damage, cardiac arrest, and ultimately death. Since the left heart is primarily responsible for circulating the flow of blood throughout the body, malfunction of the mitral valve 22 is particularly problematic and often life threatening.

Methods for repairing a target organ tissue, such as repair of mitral valve leaflets to address mitral valve regurgitation, includes inserting a delivery device, such as a delivery device described in the see, e.g., PCT Application No. PCT/US2012/043761, (published as WO 2013/003228 A1, and referred to herein as "the '761 PCT Application") and/or in PCT Application No. PCT/US2016/055170 (published as WO 2017/059426A1 and referred to herein as "the '170 PCT Application"), the entire disclosure of each of which is incorporated herein by reference, into a body and extending a distal end of the delivery device to a proximal side of the tissue. Advancement of the delivery device may be performed in conjunction with sonography or direct visualization (e.g., direct transblood visualization), and/or any other suitable remote visualization technique. With respect to cardiac procedures, for example, the delivery device may be advanced in conjunction with transesophageal (TEE) guidance or intracardiac echocardiography (ICE) guidance to facilitate and to direct the movement and proper positioning of the device for contacting the appropriate target cardiac region and/or target cardiac tissue (e.g., a valve leaflet, a valve annulus, or any other suitable cardiac tissue). Typical procedures for use of echo guidance are set forth in Suematsu, Y., J. Thorac. Cardiovasc. Surg. 2005; 130:1348-56 ("Suematsu"), the entire disclosure of which is incorporated herein by reference.

As described in detail in the '761 PCT Application and the '170 PCT Application, methods and devices are provided for performing non-invasive procedures to repair a cardiac valve, such as a mitral valve. Such procedures include procedures to repair regurgitation that occurs when the leaflets of the mitral valve do not coapt at peak contraction pressures, resulting in an undesired back flow of blood from the ventricle into the atrium. As described in the '761 PCT Application and the '170 PCT Application, after the malfunctioning cardiac valve has been assessed and the source of the malfunction verified, a corrective procedure can be performed. Various procedures can be performed in accordance with the methods described therein to effectuate a cardiac valve repair, which will depend on the specific abnormality and the tissues involved.

After prepping and placing the subject under anesthesia, a transesophageal echocardiogram (TEE) (2D and/or 3D), a transthoracic echocardiogram (TTE), intracardiac echo (ICE), or cardio-optic direct visualization (e.g., via infrared vision from the tip of a 7.5 F catheter) may be performed to assess the heart and its valves.

After a minimally invasive approach is determined to be advisable, one or more incisions are made proximate to the thoracic cavity to provide a surgical field of access. The total number and length of the incisions to be made depend on the number and types of the instruments to be used as well as the procedure(s) to be performed. The incision(s) should be made in such a manner to be minimally invasive. As referred to herein, the term minimally invasive means in a manner by which an interior organ or tissue may be accessed with as little as possible damage being done to the anatomical structure through which entry is sought. Typically, a minimally invasive procedure is one that involves accessing a body cavity by a small incision of, for example, about 5 centimeter (cm) or less made in the skin of the body. The incision may be vertical, horizontal, or slightly curved. If the incision is placed along one or more ribs, it should follow the outline of the rib. The opening should extend deep enough to allow access to the thoracic cavity between the ribs or under the sternum and is preferably set close to the rib cage and/or diaphragm, dependent on the entry point chosen.

In one example method, the heart may be accessed through one or more openings made by a small incision(s) in a portion of the body proximal to the thoracic cavity, for example, between one or more of the ribs of the rib cage of a patient, proximate to the xyphoid appendage, or via the abdomen and diaphragm. Access to the thoracic cavity may be sought so as to allow the insertion and use of one or more thorascopic instruments, while access to the abdomen may be sought to allow the insertion and use of one or more laparoscopic instruments. Insertion of one or more visualizing instruments may then be followed by transdiaphragmatic access to the heart. Additionally, access to the heart may be gained by direct puncture (e.g., via an appropriately sized needle, for instance an 18-gauge needle) of the heart from the xyphoid region. Accordingly, the one or more incisions should be made in such a manner as to provide an appropriate surgical field and access site to the heart in the least invasive manner possible. Access may also be achieved using percutaneous methods further reducing the invasiveness of the procedure. See, for instance, "Full-Spectrum Cardiac Surgery Through a Minimal Incision Mini-Sternotomy (Lower Half) Technique," Doty et al., Annals of Thoracic Surgery 1998; 65(2): 573-7 and "Transxiphoid Approach Without Median Stermotomy for the Repair of Atrial Septal Defects," Barbero-Marcial et al., Annals of Thoracic Surgery 1998; 65(3): 771-4, the entire disclosures of each of which are incorporated herein by reference.

Once a suitable entry point has been established, the surgeon can use one or more sutures to make a series of stiches in one or more concentric circles in the myocardium at the desired location to create a "pursestring" closure. The Seldinger technique can be used to access the left ventricle in the area surrounded by the pursestring suture by puncturing the myocardium with a small sharp hollow needle (a "trocar") with a guidewire in the lumen of the trocar. Once the ventricle has been accessed, the guidewire can be advanced, and the trocar removed. A valved-introducer with dilator extending through the lumen of the valved-introducer can be advanced over the guidewire to gain access to the left ventricle. The guidewire and dilator can be removed and the valved-introducer will maintain hemostasis, with or without a suitable delivery device inserted therein, throughout the procedure. Alternatively the surgeon can make a small incision in the myocardium and insert the valved-introducer into the heart via the incision. Once the valved-introducer is properly placed the pursestring suture is tightened to reduce bleeding around the shaft of the valved-introducer.

A suitable device such as a delivery device described in the '761 PCT Application and/or the '170 PCT Application, may be advanced into the body and through the valved-introducer in a manner so as to access the left ventricle. The advancement of the device may be performed in conjunction with sonography or direct visualization (e.g., direct trans-blood visualization). For example, the delivery device may be advanced in conjunction with TEE guidance or ICE to facilitate and direct the movement and proper positioning of the device for contacting the appropriate apical region of the heart. Typical procedures for use of echo guidance are set forth in Suematsu.

The delivery device described in the in the '761 PCT Application and/or the '170 PCT Application can be used to deliver one or more sutures onto a mitral valve leaflet using minimally invasive techniques. A suture or a pair of sutures with a suture knot at a distal end can be delivered into the left ventricle where the suture knot can be deployed onto the mitral valve leaflet, coupling the suture or pair of sutures to the mitral valve leaflet. A proximal portion of the suture or pair of sutures (suture tails) can be secured to the outer ventricular wall of the heart. The length of the suture or pair of sutures within the ventricle can be adjusted, such as under real-time TEE guidance to observe response of the mitral valve leaflet, prior to securing the proximal portion to the outer ventricular wall of the heart. Tension can be applied to the suture or pair of sutures to adjust the length of the suture or pair of sutures, for example by manipulation of portions of the suture or pair of sutures extending externally from the heart, so as to achieve desired mitral valve leaflet coaptation behavior.

Applying too much tension to a suture or pair of sutures coupled to a target organ tissue can result in damage to the target organ tissue and/or undesired immobilization of the target organ tissue. As described herein, an operator can apply force upon a suture or pair of sutures deployed onto a mitral valve leaflet to determine the response of the mitral valve leaflet to the tension applied to suture. For example, tension can be applied upon the suture or pair of sutures to determine the effect upon leaflet coaptation and reduction on valve regurgitation. To reduce or eliminate mitral valve regurgitation, the operator can adjust the tension applied upon the suture or pair of sutures by adjusting the length of the suture used to tether the mitral valve leaflet to the wall of the heart based on the response of the mitral valve leaflet, for example under echo guidance. Tensioning of each suture or pair of sutures deployed onto the mitral valve leaflet can be performed by an operator to select an appropriate number of sutures (e.g., suture knots) to deploy onto the mitral valve leaflet, appropriate level of tension for each of the sutures or pair of sutures, and/or positioning of any subsequent sutures deployed onto the mitral valve leaflet, so as to achieve desired mitral valve leaflet behavior. Tensioning of individual sutures or pair of sutures to determine their respective effect upon leaflet prolapse can be useful to correctly select the number and/or positioning of subsequent sutures so as to adequately repair mitral valve regurgitation.

Certain practices involve the operator clamping together into one group an external portion of all sutures deployed onto the mitral valve leaflet, rendering identification of individual sutures or pairs of sutures and individual tensioning of the sutures or pairs of sutures difficult. In working with multiple sutures, which all can have the same or a similar appearance, the operator may have trouble reliably and quickly identifying the desired suture during a procedure. The clamp may cause damage to tissue adjacent to where the clamp is applied. A corresponding number of knots tied on a portion of each suture or pair of sutures external to the heart for identification of the individual sutures may be small and difficult to see. Blood spilled on the sutures can further blur the surgical field and complicate identification of the sutures.

Clamping together of the sutures can prevent individual tensioning of the sutures. The operator may inadvertently over tension a suture. Applying too much tension to a suture or pair of sutures can result in leaflet rupture, migration of the suture, and/or complete dislodging of the suture from the leaflet. In some cases, over tensioning the suture can result in undesired immobilization of the leaflet, preventing correct functioning of the leaflet. Directly manipulating the sutures may be challenging due to the number of sutures which can be present, and the thinness of the sutures. Incorrect identification of the pair of sutures corresponding to a particular suture deployed to the mitral valve leaflet can cause mischaracterization of mitral valve leaflet behavior, which can result in miscalculations in subsequent deployment of sutures and/or incorrect tensioning of the pair of sutures.

One or more methods and/or devices described herein can facilitate desired tensioning and/or identification of individual sutures or pairs of sutures deployed onto a target organ tissue, such as a mitral valve leaflet. A label can be applied to at least a portion of a suture or a pair of sutures which extends externally from the heart. For example, a portion of a suture or pair of sutures, which is deployed to a mitral valve leaflet, extending externally of the heart can be labeled by an operator to facilitate quick and reliable visual identification of the suture or pair of sutures. In some examples, the label can comprise a distinguishing color applied to the portion of the suture or pair of sutures. For example, an operator may use label applicators of various colors, such as a coloring marker, to apply a distinguishing color to each individual suture. Any number of inks safe for surgical applications can be used, such as methylene blue. In some examples, the visually distinguishing label can comprise a label other than a color, such as a pattern, applied to at least a portion of the suture or pair of sutures extending externally of the heart. Examples disclosed herein provide for the engaging of suture tabs and/or tension guides atraumatically substantially without creasing, crimping, compressing or clamping onto the suture(s). Furthermore, examples disclosed herein provide the ability to simultaneously tension a plurality of deployed sutures and adjust tension independently relative to the other sutures to determine the best combination to achieve optimum results.

In some examples, a suture tab can be attached to a portion of a suture or pair of sutures extending externally of the heart to facilitate manipulation of the suture. The suture tab can comprise a grip portion having a shape and/or size to enable ease of gripping by the operator. The suture tab can comprise a suture engagement feature configured to securely receive the portion of the suture or pair of sutures. In some examples, the suture engagement feature can comprise a pair of opposing notches on the suture tab around which the portion of the suture or pair of sutures can be wound such that the suture can securely couple to the suture tab. In some examples, the suture engagement feature can comprise a different configuration, such as a hook, a knob, and/or any other feature which can securely receive a portion of the suture or pair of sutures. The operator can grip the suture tab to manipulate the suture rather than directly manipulate the suture. For example, the operator can apply a force upon the suture by manipulating the suture tab instead of gripping the suture or pair of sutures itself.

In some examples, the suture tab may be labeled for easy visual identification, such as via a color and/or an alphanumeric label. In some examples, the suture tab can be used in combination with the label applicator to facilitate quick and reliable identification of sutures, as well as easy manipulation of the sutures. In some examples, the suture tab and/or the label applicator can be used independently of one another. For example, the suture tab can be used without the label applicator, where the suture tab can both facilitate visual identification of individual sutures and to provide ease of handling of the sutures. In some examples, the label applicator can be used without the suture tab.

In some examples, an operator can use a tension guide to prevent applying too much tension to a suture or pair of sutures. The tension guide may comprise an engagement portion configured to engage with a portion of a suture or pair of sutures extending externally of the target organ, such as the heart. In some examples, the engagement portion can engage directly with the suture or pair of sutures. In some examples, the engagement portion may engage with a suture tag, for example a suture tab coupled to the portion of the suture extending externally of the heart. The tension guide can provide visual guidance to the operator regarding whether too much force is being applied to the suture or pair of sutures while the operator tensions the suture to determine a response of the mitral valve leaflet. For example, the tension guide can be configured to serve as a safety gauge to alert the operator when too much force is applied and over-tensioning of the suture or pair of sutures may occur.

In some examples, the tension guide may be used in combination with the label applicator and/or the suture tab. In some examples, the tension guide can be used independently of the label applicator and the suture tab.

It will be understood that although methods and devices described herein refer to a suture or pair of sutures, the methods and devices can be applicable to any number of sutures which correspond to a suture knot deployed to a target organ tissue, such as the mitral valve leaflet.

Figure 4B:
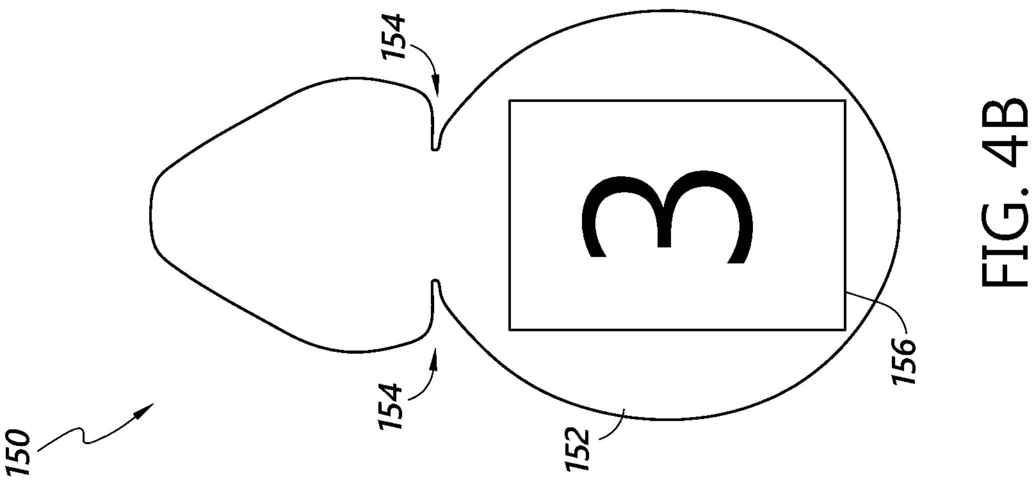
FIG. 4B shows an example of a suture tab.
Figure 4A:
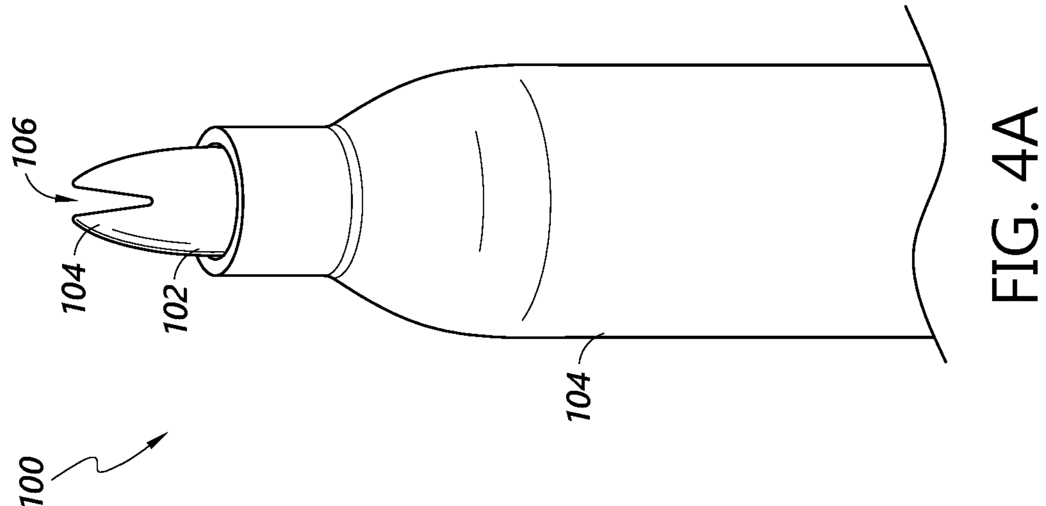
FIG. 4A shows an example of a label applicator.

FIG. 4A shows an example of a coloring marker 100. The coloring marker 100 can have a handle 104 to facilitate gripping of the coloring marker 100 by an operator, and an applicator 102 extending therefrom. The applicator 102 can be configured to apply a desired color to sutures. The applicator 102 can have a tip portion 106 comprising an applicator groove 106. Although a groove is described and shown in connection with certain examples, it should be understood that applicator tips in accordance with the present disclosure may comprise hook, flute, notch, loop, slit, or other type of suture-receiving feature or element. The applicator groove 106 can be configured to receive a segment of one or more sutures to be colored by the coloring marker 100. For example, a segment of a suture or a pair of sutures can be positioned within the groove 106 and the operator can then move the applicator 106 along a desired length of the suture or pair of sutures with the suture or pair of sutures positioned within the groove to apply the color thereon. The applicator groove 106 can be sized so as to securely receive the segment of the one or more sutures while the applicator 106 is moved along the length of the suture or pair of sutures. The sutures can be securely received within the groove 106 to prevent accidental smearing of other sutures.

FIG. 4B shows an example of a suture tab 150. The suture tab 150 can have a grip 152 configured to facilitate gripping by an operator, and a pair of notches 154 configured to receive a portion of one or more sutures. For example, a segment of a suture or a pair of sutures can be wound around the suture tab 150 such that portions of the suture can be received within the pair of notches 154 to facilitate securing of the suture tab 150 to the suture or pair of sutures. The suture tab 150 may serve to facilitate manipulation of one or more sutures, for example enabling ease of handling of the one or more sutures. The grip 152 may be sized and/or shaped to facilitate holding of the suture tab 150 between an operator's fingers, such as by the operator's fingertips. Although certain suture tab forms are illustrated and described herein, it should be understood that suture tabs in accordance with the present disclosure can have any suitable or desirable form, feature(s), configuration, and or means for receiving or coupling sutures, such as a post, series of posts, or other element or means of atraumatically securing suture (s) to the tab.

In some examples, the operator may want to apply a force upon a suture or pair of sutures deployed onto a mitral valve leaflet to determine a response of the mitral valve leaflet to the tension applied upon the pair of sutures. Rather than attempting to grip the pair of sutures directly, the operator can wrap a portion of the suture or pair of sutures around the pair of notices 154 of the suture tab 150 to secure the suture or pair of sutures around the suture tab 150. The operator can then hold onto the suture tab 150 when manipulating the suture or pair of sutures and to apply the desired tension upon the suture or pair of sutures. The pair of sutures can be secured to a portion of the heart wall after the operator determines that an appropriate amount of tension has been applied, such as secured to an anchor (e.g., pledget) on the exterior of the heart. The suture tab 150 thereby can facilitate application of tension to individual sutures or pairs of sutures and individually securing the suture or pair of sutures.

The suture tab 150 may comprise one or more identifying features to distinguish it from other suture tags used in a procedure. In some examples, the tab 150 can comprise a distinguishing color. In some examples, the suture tab 150 can comprise an alphanumeric label 156. For example, the suture tab 156 shown in FIG. 4B can comprise a number. In some examples, the suture tab 150 can have an identifying color and an identifying alphanumeric label. The suture tab 150 can have any number of identifying features to allow an operator to easily and quickly identify the desired suture during a procedure.

A suture tab can comprise any number of materials. The suture tab can be compact and made with lightweight material to facilitate its use in surgical procedures. In some examples, the suture tab can comprise a polymeric material.

In some examples, one or more coloring markers can be used in combination with one or more suture tags described herein. For example, for ease of identifying and handling of a pair of sutures, an operator can couple a suture tab to the pair of sutures, and a coloring marker can be used to apply an identifying color to the pair of sutures.

In some examples, as described in further detail herein, a suture tab can be configured to engage with one or more tension guides described herein. For example, the suture tab can have one or more features to engage with an engagement portion of a tension guide. Tension applied to sutures can be applied via the tension guide coupled to the suture tab.

Figure 5:
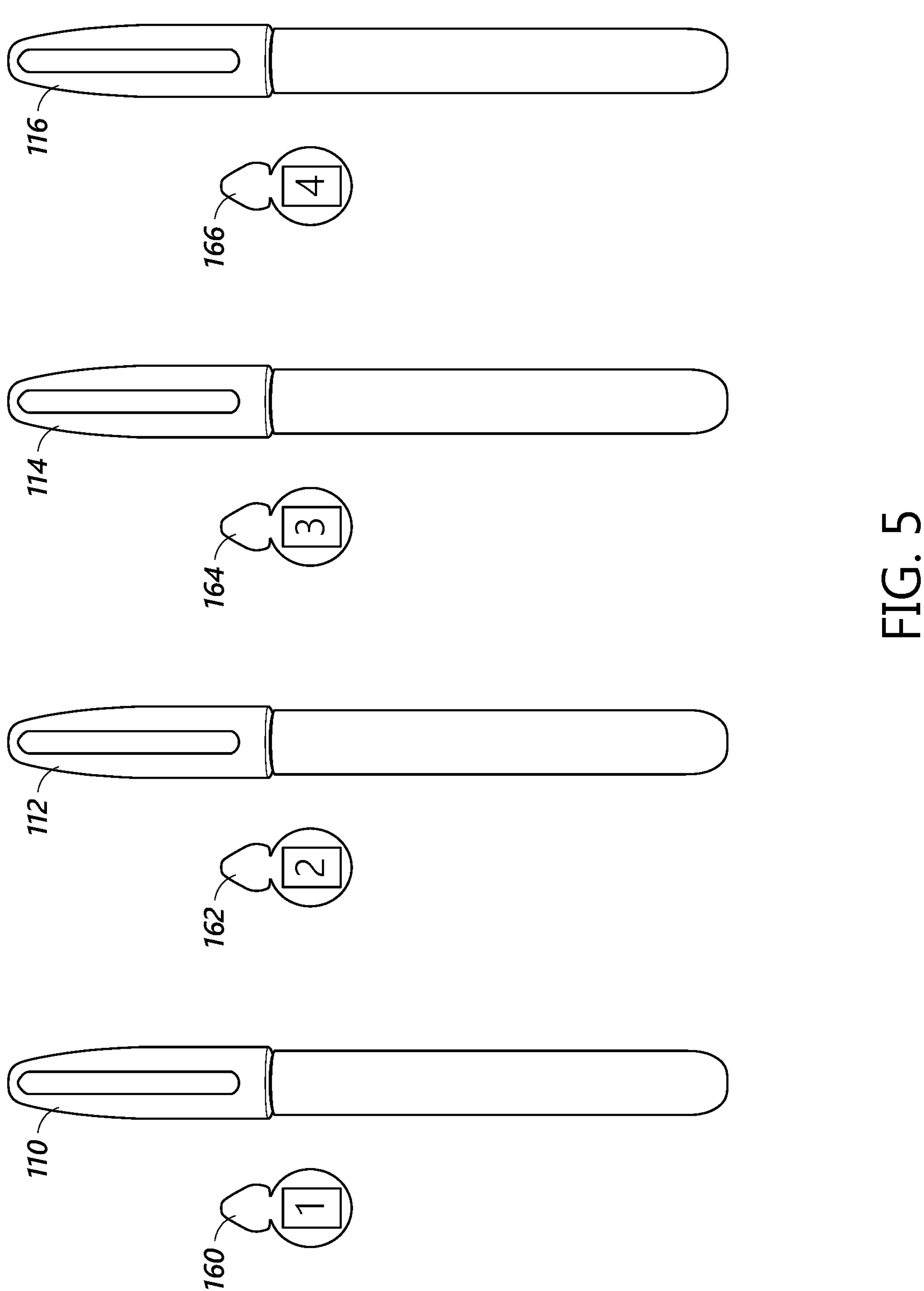
FIG. 5 shows examples of label applicators and suture tags.

FIG. 5 shows four coloring markers 110, 112, 114, 116, and four suture tags 160, 162, 164, 166, which can be used in combination to facilitate both identification and handling of sutures. For example, each of the four coloring markers can be paired with one of the four suture tags 160, 162, 164, 166 such that an operator can both apply an identifying color to a pair of sutures and tab the colored pair of sutures with a corresponding suture tab. The first coloring marker 110 can be paired with the first suture tab 160, the second coloring marker 112 can be paired with the second suture tab 162, third coloring marker 114 can be paired with the first suture tab 164, and third coloring marker 116 can be paired with the first suture tab 166. In some examples, a suture tab can have the same color as the coloring marker to which it is paired. In some examples, a suture tab and the coloring marker to which it is paired does not share a color. For example, the suture tab can have the same color as other suture tags but can have another identifying feature to distinguish it from other suture tags, such as an alphanumeric label.

Figure 6B:
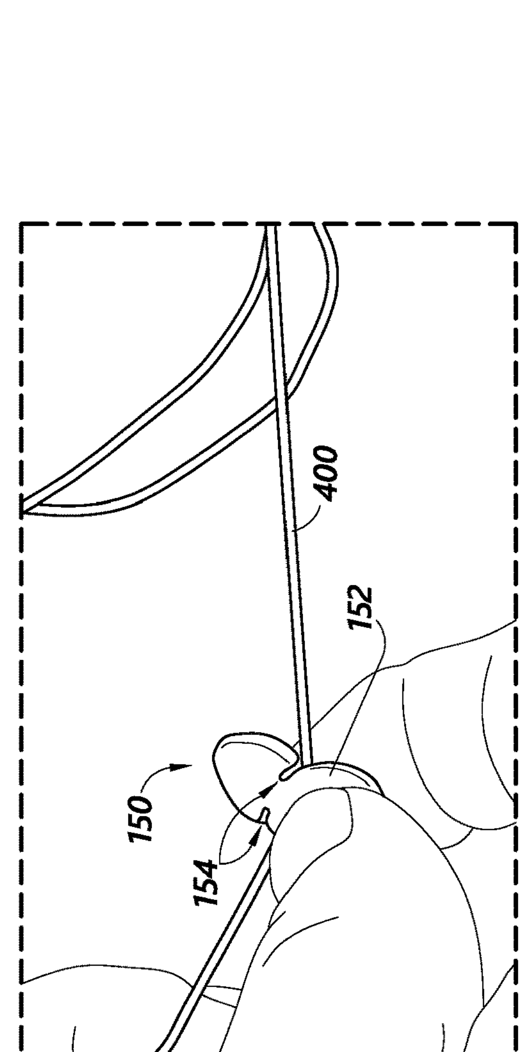
Figure 6B:
Figure 6D:
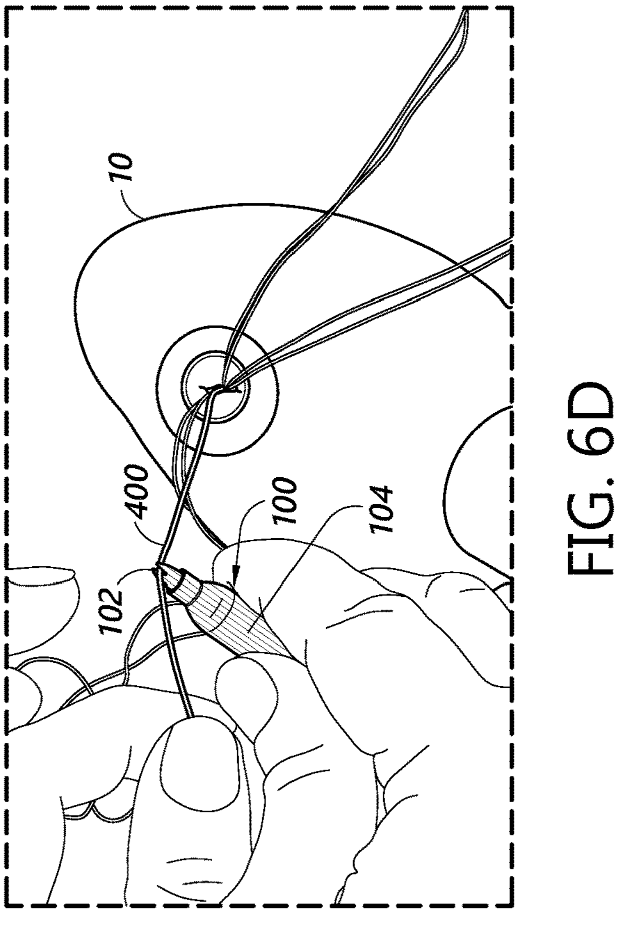
Figure 6C:
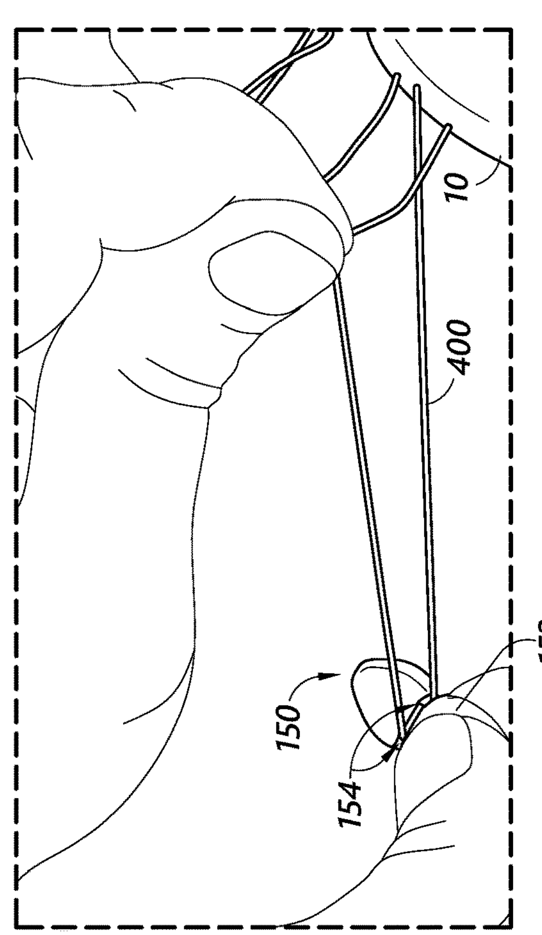
Figure 6E:
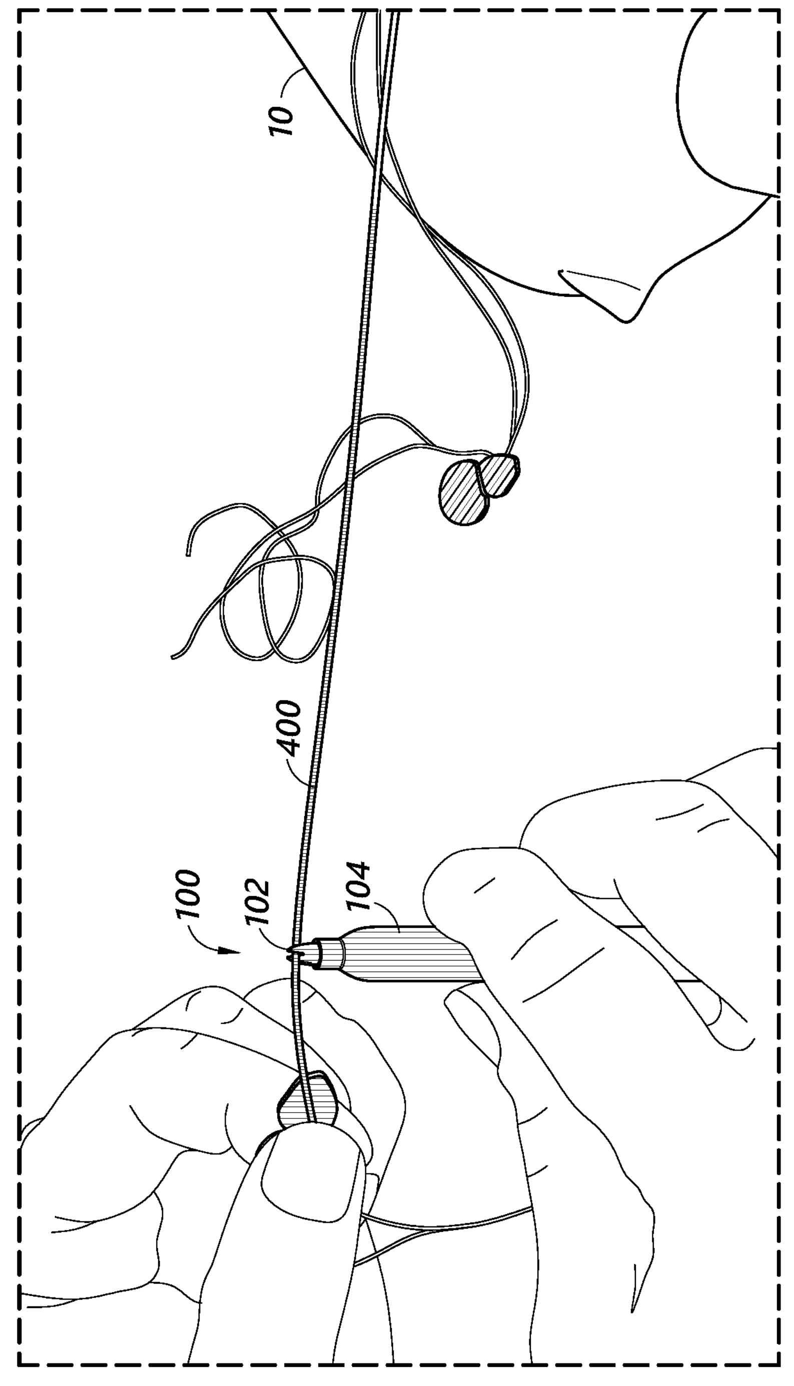

FIGS. 6A through 6E show an example of an operator attaching a suture tag, such as the suture tab 150, onto a pair of sutures 400 and coloring the pair of sutures, for example using the coloring marker 100. For example, the pair of sutures 400 have a distal portion deployed onto a mitral valve leaflet within the heart 10. As shown in FIGS. 6A through 6C, the operator can attach the suture tab 150 to a portion of a free end of the pair of sutures 400 external to the heart 10. The operator can wind a portion of the free end of the pair of sutures 400 around the notch portion 154 of the suture tab 150. While winding the pair of sutures 400 around the suture tab 150, the operator can hold onto the grip 152. In FIGS. 6D and 6E, the operator is shown holding onto the coloring marker 100 by its handle 104 and applying the applicator 102 of the coloring marker 100 to the pair of sutures 400 to add a color to the pair of sutures 400. The operator can move the coloring marker 100 along at least a portion of the length of the pair of sutures 400 extending externally of the heart 10 so as to label the pair of sutures 400 with the color of the coloring marker.

Figure 7:
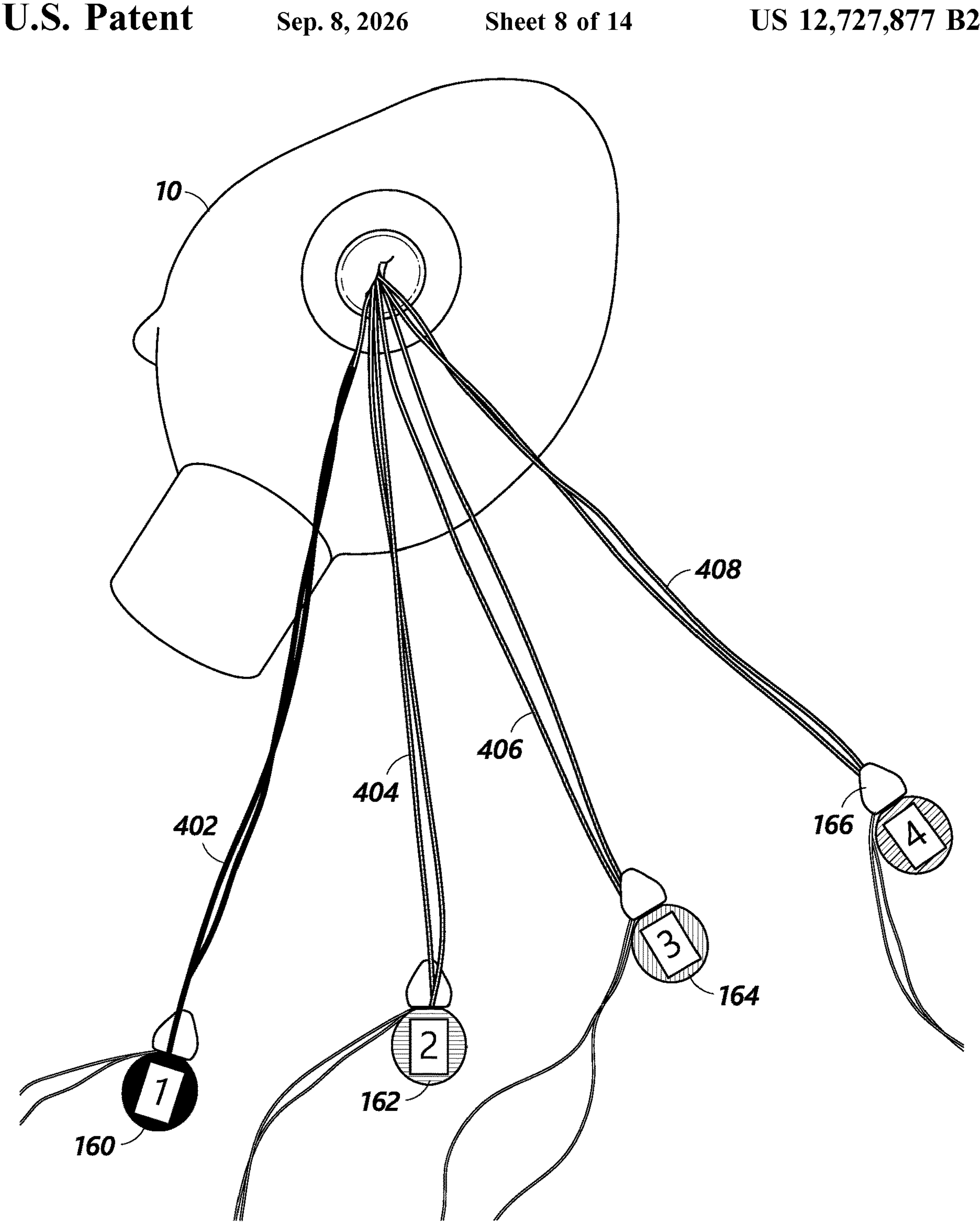
FIG. 7 shows an example of four pairs of sutures each of which is both labeled with a distinguishing color and suture tab.

In some examples, the process as described with reference to FIGS. 6A through 6E can be repeated with a desired number of pairs of sutures. For example, as shown in FIG. 7, portions of four pairs of sutures 402, 404, 406, 408, extending externally of a heart 10 can each be labeled using a corresponding coloring marker and coupled to a corresponding suture tab. For example, the coloring markers 110, 112, 114, 116 and suture tags 160, 162, 164, 166 described with reference to FIG. 5 can be used.

In some examples, a suture tab can both provide ease of handling of sutures and quick identification of sutures. In some examples, a suture tab may not have individual identifying features. For example, suture tags can be used in combination with coloring markers such that the coloring markers can provide ease of identification of the sutures while the suture tags can provide ease of handling of the sutures.

As described herein, a tension guide can provide a visual indicator for an operator to inform the operator regarding whether tension applied to a suture or pair of sutures via the tension guide is within a safe range. The tension guide can provide visual guidance regarding whether force applied upon the suture or pair of sutures can result in damage to the target organ tissue, for example preventing damage to a mitral valve leaflet. The tension guide can comprise an engagement portion and an elastic mechanical energy storage. The engagement portion can be configured to engage directly or indirectly with a portion of a suture or pair of sutures. The engagement portion can be coupled to the elastic mechanical energy storage such that the elastic mechanical energy storage can deform when a mechanical force is applied upon the engagement portion, such as by pulling on the suture or pair of sutures.

The tension guide can be configured to allow the operator to observe an indicator indicative of the degree of deformation of the elastic mechanical energy storage such that the operator can readily determine whether force applied upon the suture or pair of sutures is within a safe range. In some examples, the tension guide can comprise visual markers on a portion of the tension guide housing to enable the operator to observe whether deformation of the elastic mechanical energy storage is within a safe range. For example, deformation of the elastic mechanical energy storage can be viewed by the operator and the tension guide housing can comprise markings (e.g., colored, patterned and/or alphanumeric markings) along a length to indicate whether deformation of the elastic mechanical energy storage is within a desired range. In some examples, the indicator can comprise an indicator other than a manual indicator, for example a digital indicator which digitally indicates to the operator whether force applied is within a desired range, with or without the operator being able to view the deformation of the elastic energy storage directly. For example, deformation of the elastic mechanical energy storage can be converted to a digital indicator displayed to the operator such that the operator can quickly understand whether force applied upon the suture or pair of sutures is acceptable.

In some examples, the elastic mechanical energy storage comprises a mechanical spring. The spring be calibrated to exhibit deformation based on the acceptable range of tension applied thereupon. For example, the spring may comprise a spring constant selected based on the acceptable range of tension. Although the elastic mechanical energy storage is described herein as comprising a mechanical spring, it will be understood that other types of elastic mechanical energy storage mechanisms can also be applicable.

One or more tension guides described herein can be used by an operator when determining the response of a target organ tissue to tension applied to one or more sutures deployed to the target organ tissue. For example, when determining the response of a mitral valve leaflet to the tension applied upon a suture or pair of sutures, the operator can monitor the indicator viewable on the tension guide. The operator may evaluate whether desired mitral valve leaflet coaptation is achieved with the applied tension, for example under echo guidance, while monitoring whether the applied tension is acceptable. The operator can observe whether the indicator indicates that the degree of deformation of the elastic mechanical storage is within a safe range that will not likely result in damage to the mitral valve leaflet. While the operator adjusts the tension applied to the suture or pair of sutures, readily available visual indication of the degree of deformation of the elastic mechanical storage can prevent the operator from applying too much tension to the suture or pair of sutures. The tension guide can serve as a safety gauge for determining whether tension applied to the suture or pair of sutures is acceptable, without undue risk of suture migration, mitral valve leaflet tear and/or mitral valve leaflet rupture. The suture or pair of sutures can then be secured to a portion of the heart after the operator determines that an appropriate amount of tension has been applied, such as to an anchor (e.g., pledget) on the exterior of the heart. Sutures or pairs of sutures can thereby be individually tensioned and secured.

Figures 8, 9:
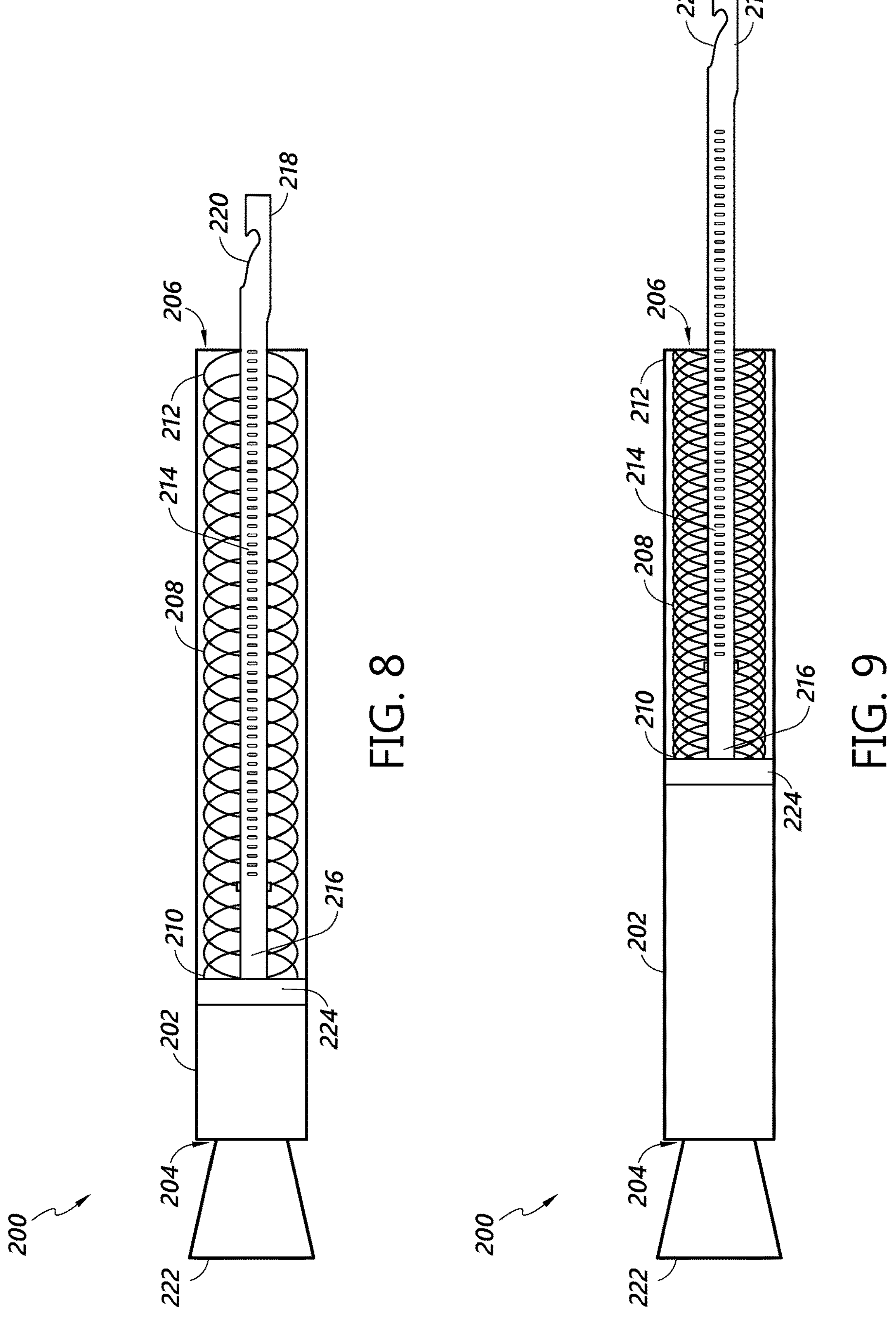
FIG. 8 is a side cross-sectional view of an example of a tension guide in a first position.
FIG. 9 is a side cross-sectional view of the tension guide shown in FIG. 8 in a second position.

Referring to FIG. 8, a side cross-sectional view is shown of a tension guide 200, where the tension guide 200 comprises a spring 208 in a first position. The tension guide 200 can comprise a tension guide housing 202 in which the spring 208 is positioned. FIG. 8 shows the spring 208 in a resting position. The tension guide housing 202 can have a proximal end 204 and a distal end 206. In some examples, the tension guide housing 202 can have a cylindrical shape. Other shapes can be applicable. Compression of the spring 208 can result in movement of a proximal end 210 of the spring 208 back and forth within the tension guide housing 202. For example, compression of the spring 208 can cause the proximal end 210 to move along a path parallel or substantially parallel to a length of the tension guide housing 202. In some examples, the proximal end 210 can be positioned against a movable surface, such as a movable disc 224 housed within the tension guide housing 202. The movable disc 224 can be configured to move back and forth within the housing 202 along the length of the housing 202. The distal end 212 of the spring 208 can be immobile, for example being positioned against an immobile surface within the tension guide housing 202. In some examples, the distal end 212 of the spring 208 can be positioned against an inner surface of the distal end 206 of the tension guide housing 202.

The proximal end 210 of the spring 208 can be coupled to a shaft 214. For example, the movable surface against which the proximal end 210 of the spring 208 is positioned can be coupled to the shaft 214. A proximal end 216 of the shaft 214 can be coupled to the movable disc 224. The shaft 214 can have a distal end 218 which extends externally of the tension guide housing 202. An external portion of the shaft 214 can comprise an engagement portion 220. The engagement portion 220 can be at or proximate to the distal end 218 of the shaft 214. Movement of the shaft 214 in a direction toward the distal end 206 of the tension guide housing 202, such as due to force applied upon the engagement portion 220, can compress the spring 208.

The engagement portion 220 shown in FIG. 8 comprises a hook. Other configurations can be applicable. The engagement portion 220 can be configured to engage directly or indirectly with a suture or pair of sutures. In some examples, the engagement portion 220 can be configured to be coupled directly to the suture or pair of sutures. In some examples, the engagement portion 220 can be configured to engage with a suture tab (e.g., a suture tab as described herein) coupled to the suture or pair of sutures.

An engagement portion can have any number of configurations to facilitate engagement directly or indirectly with a suture or pair of sutures. In some examples, an engagement portion can be configured to be directly coupled to the engagement portion, such as by winding, tying, and/or otherwise attaching, the suture or pair of sutures onto the engagement portion. In some examples, an engagement portion can be configured to releasably receive the suture tab (e.g., hook onto, click into).

The tension guide 200 can comprise a handle 222 coupled to the proximal end 204 of the housing 202 to facilitate manipulation of the tension guide 200 by an operator. The handle 222 can have any number of configurations to provide ease of handling by the operator. In some examples, the tension guide 200 may not comprise a handle 222. For example, the operator may directly grip the tension guide housing 202.

FIG. 9 is a side cross-sectional view of the tension guide 200 in a second position. For example, FIG. 9 shows the spring 208 in a compressed state. Force applied to the shaft 214, such as via the engagement portion 220, to pull the shaft 214 in a direction toward the distal end 206 of the tension guide housing 202 can result in movement of the movable disc 224 toward the distal end 206 of the tension guide housing 202, thereby compressing the spring 208. For example, an operator can apply tension upon the suture or pair of sutures coupled to the engagement portion 220 by applying a force upon the handle 222 to pull the tension guide housing 202 toward the operator. Pulling of the tension guide housing 202 toward the operator can move the shaft 214 toward the distal end 206 of the housing 202, thereby moving the movable disc 224 toward the distal end 206 of the housing 202 and compressing the spring 208.

Figure 10:
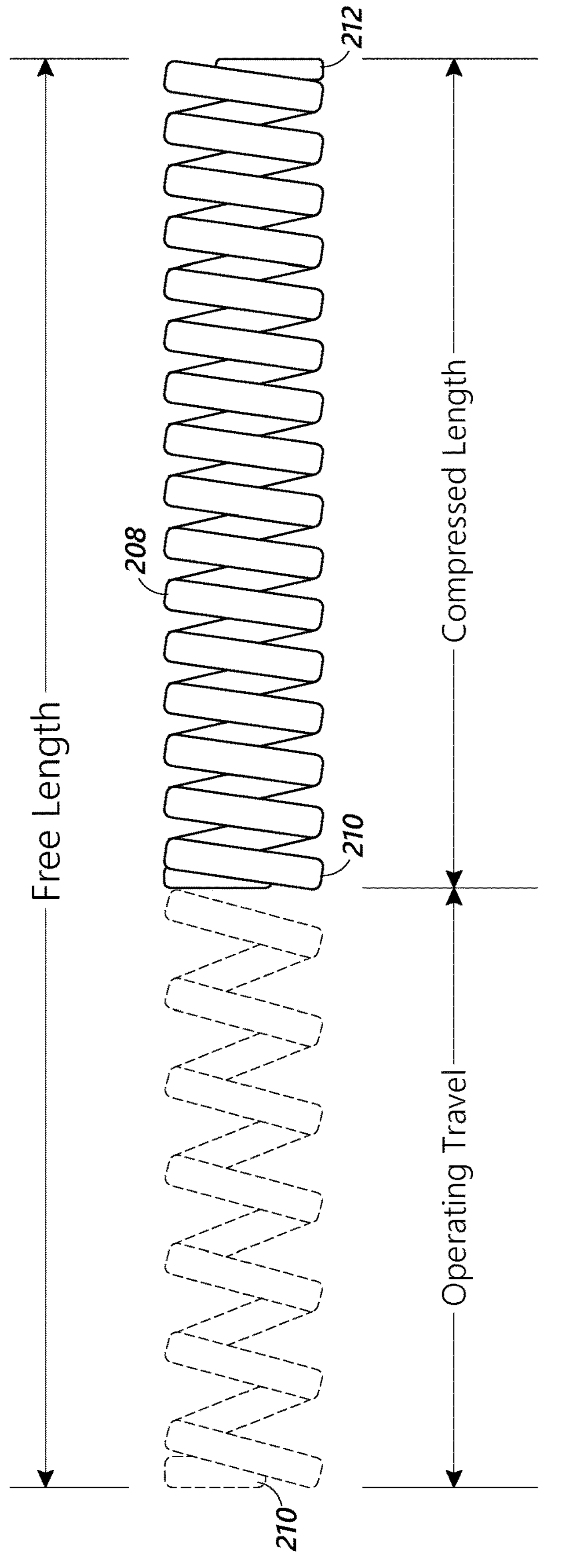
FIG. 10 shows the spring of the tension guide shown in FIG. 9 in the second position.

Referring to FIG. 10, the spring 208 can be at a free length in its resting position. An operating load applied upon the engagement portion 220 of the shaft 214 can result in movement of the proximal end 210 of the spring 208. The proximal end 210 can be displaced an operating travel length, resulting in compression of the spring 208 such that the spring 208 assumes a compressed length.

In some examples, the tension guide 200 can be configured such that the operator can view the degree to which the spring 208 is compressed to determine whether tension applied upon the suture or pair of sutures coupled to the tension guide 200 is acceptable. For example, visual markers (not shown) can be positioned along a portion of an exterior of the tension guide housing 202 to allow the operator to quickly determine whether the degree of compression of the spring 208 corresponds to a suture tension that is within a safe range.

Figure 11:
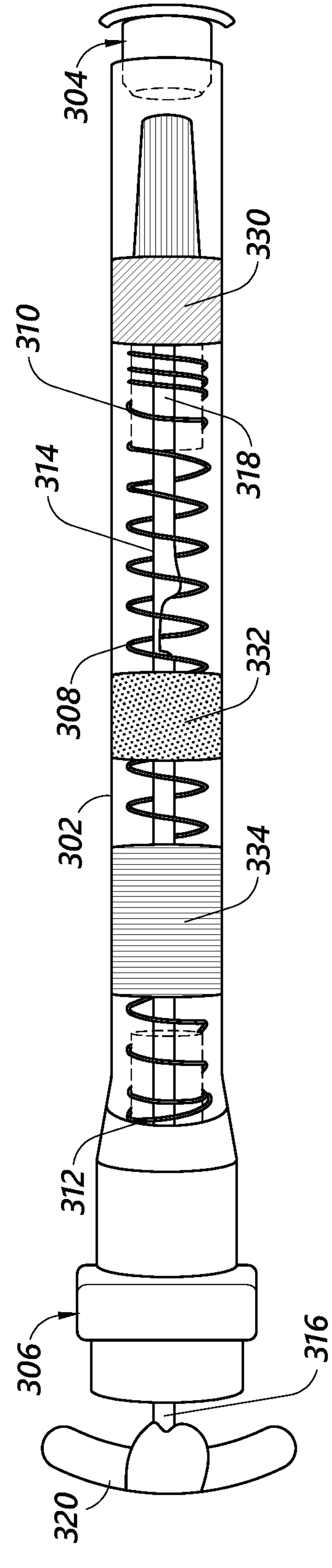
FIG. 11 is a side view of another example of a tension guide.

FIG. 11 is a side view of another example of a tension guide 300. The tension guide 300 can comprise a tension guide housing 302 in which a spring 308 is positioned. The tension guide housing 302 can have a cylindrical shape. The tension guide housing 302 can have a proximal end 304 and a distal end 306. The spring 308 can have a proximal end 310 and a distal end 312. The proximal end 310 of the spring 308 can be movable back and forth along a length of the tension guide housing 302, such as when the spring 308 is compressed and relaxed. The distal end 312 of the spring 308 can be immobile, for example being positioned against an immobile surface within the tension guide housing 302, such as an inner surface of the distal end 306 of the tension guide housing 302. The proximal end 310 of the spring 308 can be coupled to a proximal end 316 of a shaft 314. The shaft 314 can have a distal end 318 which extends externally of the tension guide housing 302, the distal end 318 comprising an engagement portion 320 for engaging with a suture or pair of sutures. For example, the suture or pair of sutures can be wound around the engagement portion 320 to secure the suture or pair of sutures to the engagement portion 320. Movement of the shaft 314 in a direction toward the distal end 306 of the tension guide housing 302 due to force applied upon the engagement portion 320 by the suture or pair of sutures can cause the proximal end 310 of the spring 308 to move toward the distal end 306 of the tension guide housing 302, compressing the spring 308.

The tension guide housing 302 can have at least a portion of which that is transparent so as to enable an operator to view the position of the spring 308. The tension guide housing 302 can be configured to allow the operator to visually assess the degree of compression of the spring 208 to determine whether the operating load applied upon the spring 308 is within a desired range. In some examples, the tension guide housing 302 can comprise only a portion of which that is transparent. In some examples, the tension guide housing 302 can be entirely or substantially entirely transparent.

In the example shown in FIG. 11, the tension guide 300 can have on an exterior of the tension guide housing 302 three color coded visual markers, a first colored label 330, a second colored label 332, and a third colored label 334. The colored labels 330, 332, 334 can be differently colored to help the operator easily distinguish between them. For example, the first colored label 330 can have a green color, the second label 332 can have a yellow color, and the third colored label 334 can have a red color. The colored labels 330, 332, 334 can be placed at predetermined positions along the length of the tension guide housing 302, with the first colored label 330 positioned closest to the proximal end 304 of the tension guide housing 302, the third colored label 334 positioned closest to the distal end 306 of the tension guide housing 302 and the second colored label 332 positioned between the first colored label 330 and third colored label 334.

As the operator pulls on the tension guide housing 302 to apply tension upon the suture or pair of sutures coupled to the engagement portion 320, the proximal end 310 of the spring 308 is moved along the length of the tension guide housing 302 toward the distal end 306 of the tension guide housing 302. The proximal end 310 of the spring 308 can move past one or more of the colored labels 330, 332, 334. Positioning of the proximal end 310 of the spring 308 between the first colored label 330 and the second colored label 332 can indicate that the force exerted upon the spring 308 is within a safe range. Positioning of the proximal end 310 of the spring 308 between the second colored label 332 and the third colored label 334 can indicate that the force exerted upon the spring 308 is within a caution range, and positioning beyond the third colored label 334 can indicate an unsafe level of force. An operator can readily visualize through the transparent portion of the tension guide housing 302 whether the force applied is within a safe range.

A tension guide can have various external visual markers to allow an operator to determine whether the operating load is within a desired range. In some examples, the visual markers can comprise a color, pattern, and/or alphanumeric marker. For example, instead of or in addition to color coded markers, a tension guide may comprise patterned and/or alphanumeric markers positioned along a portion of the tension guide housing as an indication to an operator regarding whether compression of the spring corresponds to application of tension that is within a safe range.

Figure 12A:
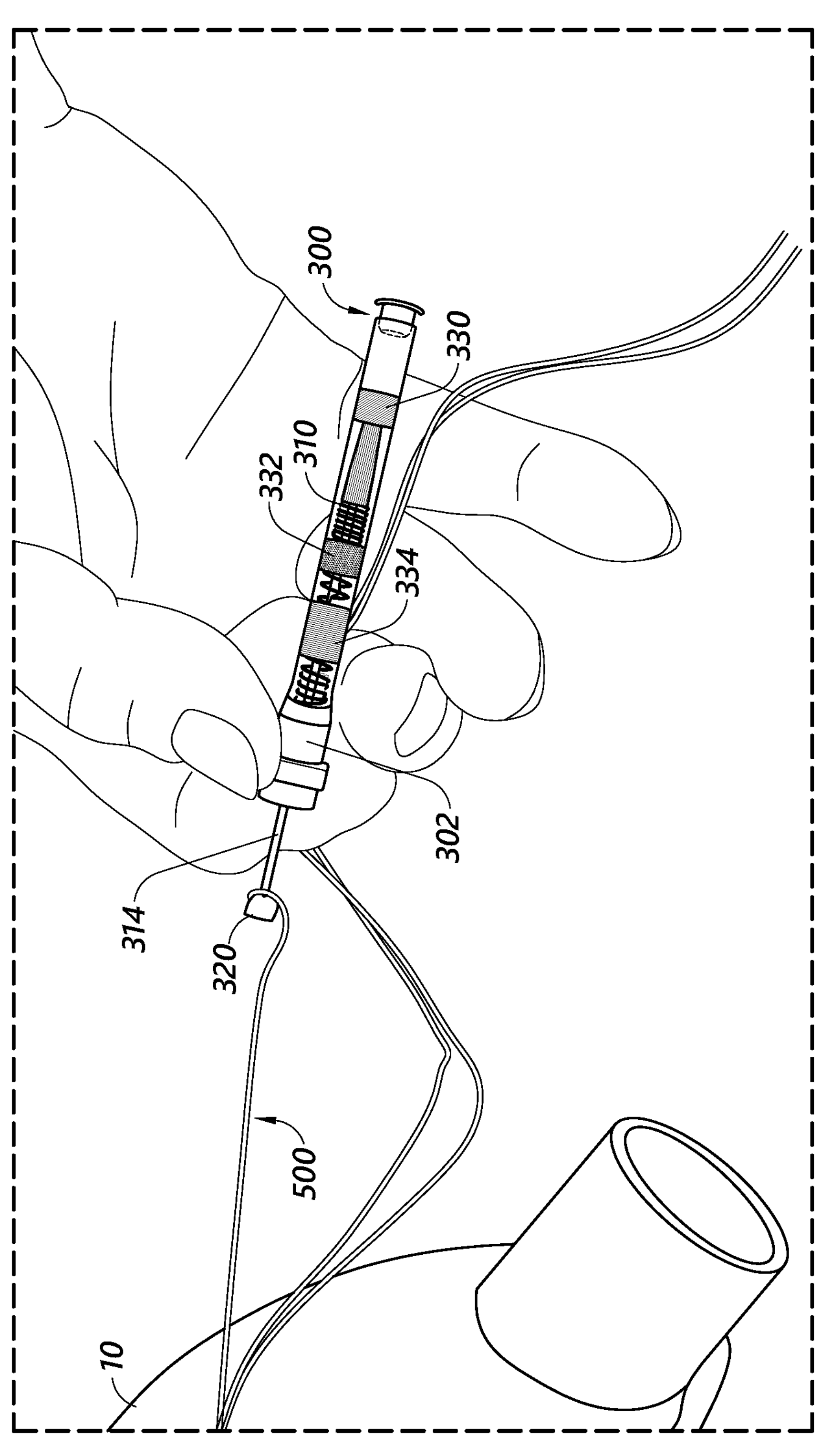
FIGS. 12A through 12C show an example of an operator using a tension guide while adjusting tension applied upon a pair of sutures.
Figure 12B:
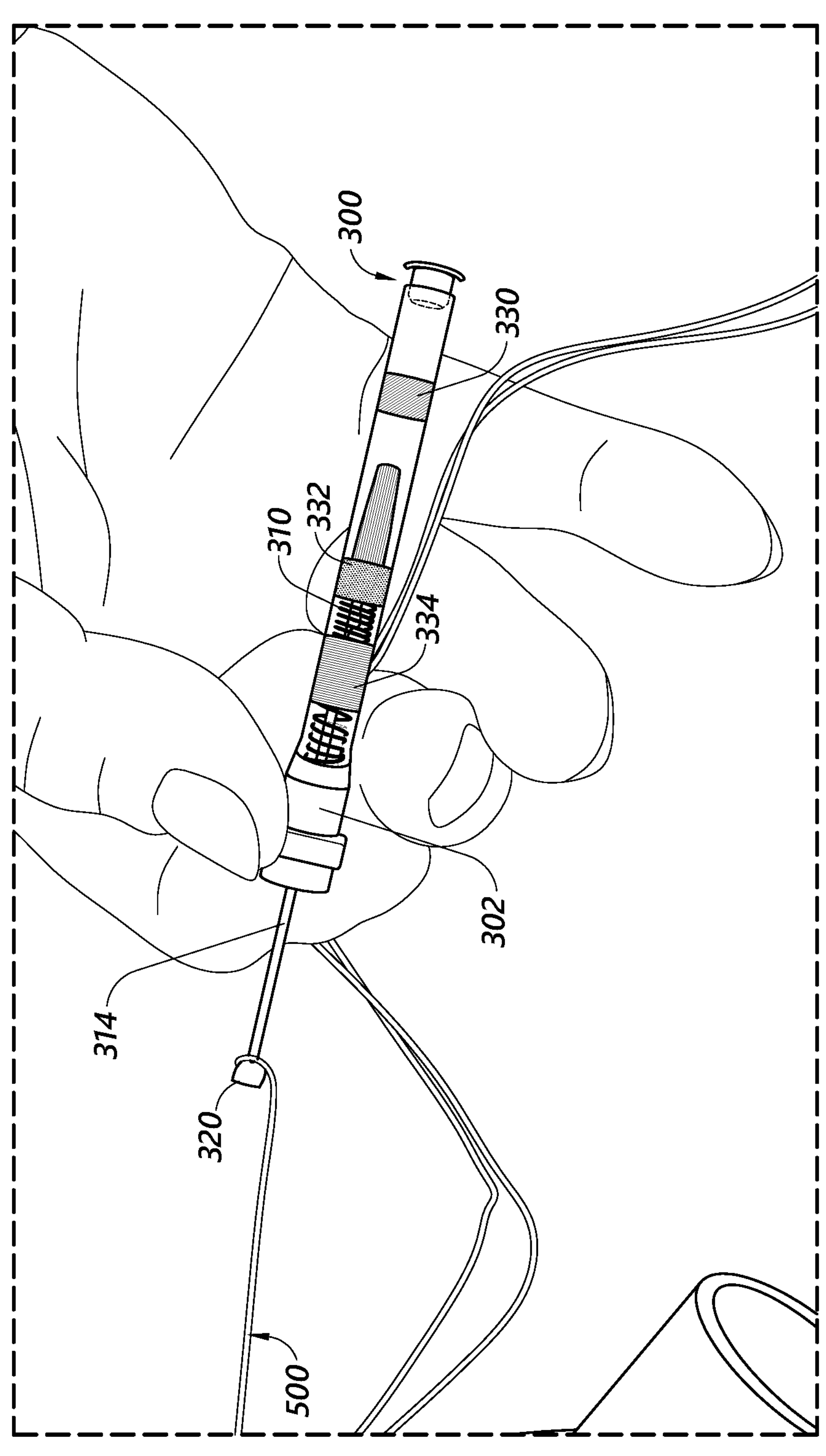
Figure 12C:
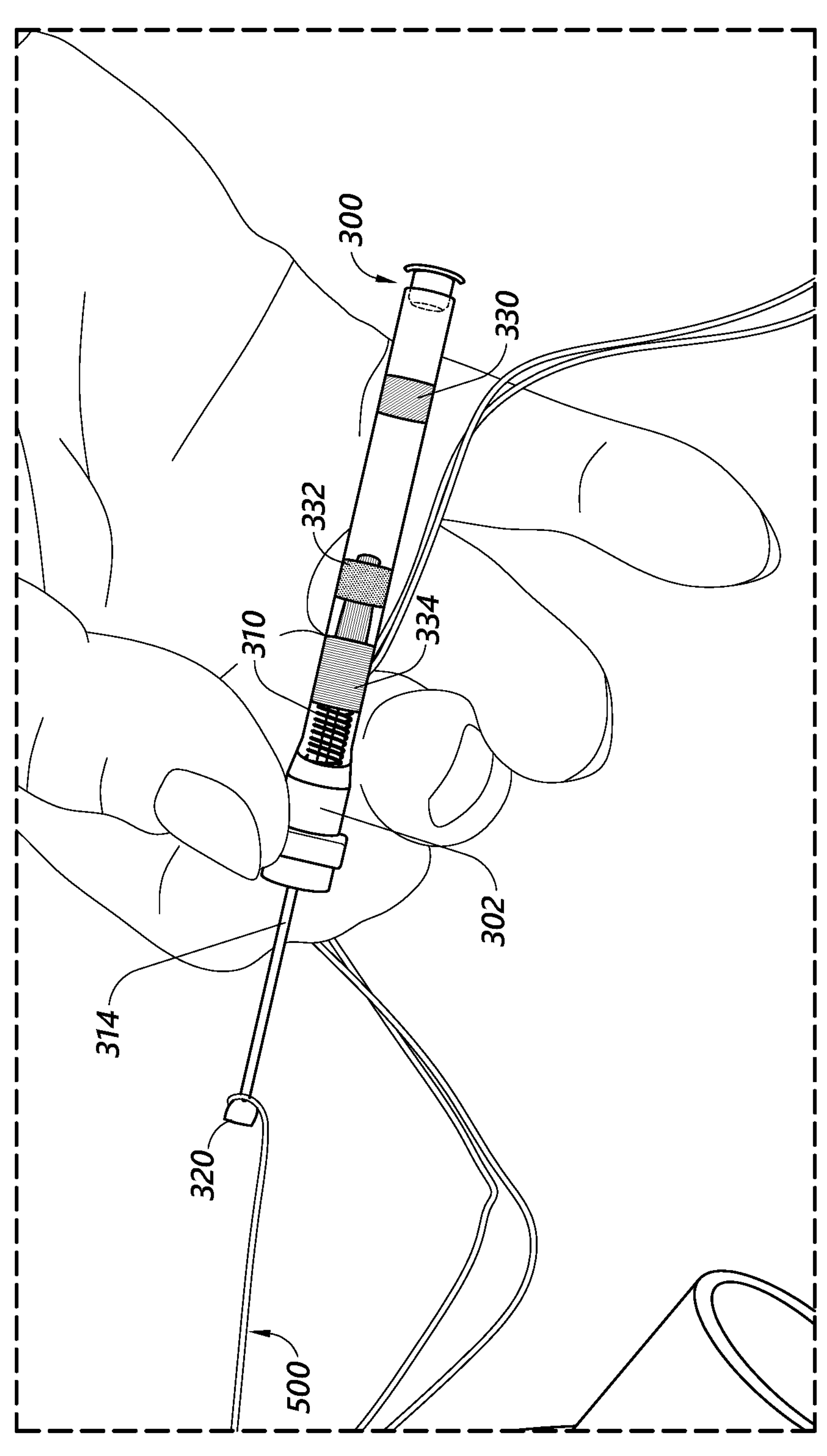

FIGS. 12A through 12C show an example of an operator using the tension guide 300 while adjusting tension applied upon a pair of sutures 500 extending externally from a heart 10. For example, the pair of sutures 500 have a distal portion deployed onto a mitral valve leaflet within the heart 10. While determining the response of the mitral valve leaflet to tension applied to the pair of sutures 500, the operator can monitor the degree to which the spring 308 is compressed. As described herein, the operator can adjust the tension applied in response to the mitral valve leaflet movement so as to determine an appropriate level of tension for desired mitral valve leaflet movement, and/or select a placement and/or number of subsequent sutures. The operator can observe whether the degree to which the spring 308 is compressed is within a safe range as marked on the tension guide housing 302.

In FIG. 12A, a portion of the pair of sutures 500 can be wound around the engagement portion 320 of the tension guide 300 and tension is applied to the pair of sutures. The proximal end 310 of the spring 308 can be positioned between the first colored label 330 and the second colored label 332, for example indicating that the tension applied to the pair of sutures 500 is within a safe range. FIG. 12B shows that the operator has further pulled on the tension guide housing 302 such that the force applied by the pair of sutures 500 coupled to the engagement portion 320 has moved the proximal end 310 of the spring 308 to or proximate to the second colored label 332. The second colored label 332 can indicate that the tension applied upon the pair of sutures 500 is entering a cautionary range. The operator can be more careful with applying any additional force once the operator observes that the second colored label 332 has been reached to ensure that the pair of sutures 500 are not over tensioned.

In FIG. 12C, the operator has pulled on the tension guide housing 302 such that the force applied to the pair of sutures 500 coupled to the engagement portion 320 has moved the proximal end 310 of the spring 308 to or proximate to the third colored label 334. The third colored label 334 can indicate that the tension applied upon the pair of sutures 500 is entering a dangerous range in which damage may be done to the mitral valve leaflet. Once the operator observes this indication, the operator should reduce the tension applied upon the pair of sutures 500, otherwise face the risk of suture displacement and/or mitral valve leaflet rupture.

The above-described procedures can be performed manually, e.g., by a physician, or can alternatively be performed fully or in part with robotic or machine assistance. For example, in some examples, a labeling applicator, suture tab and/or tension guide can be configured to be delivered and deployed automatically.

Additional Examples and Terminology

While various examples have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or examples described above indicate certain components arranged in certain orientations or positions, the arrangement of components may be modified. While the examples have been particularly shown and described, it will be understood that various changes in form and details may be made. Any portion of the apparatus and/or methods described herein may be combined in any combination, except mutually exclusive combinations. The examples described herein can include various combinations and/or sub-combinations of the functions, components and/or features of the different examples described.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various examples described above can be combined to provide further examples. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method of managing suture deployment onto target organ tissue, the method comprising:

providing a tension guide device including:

a tubular housing including a transparent sidewall portion;

an elongate rod disposed partially within the tubular housing, the elongate rod terminating at a proximal end with a stopper disc tension marker slidingly disposed within the tubular housing, and terminating at a distal end with a suture-engagement hook associated with a distal portion of the elongate rod that passes through an aperture in a distal endcap of the housing, such that the suture-engagement hook is disposed distally external to the housing;

a spring disposed about the elongate rod, the spring abutting the stopper disc tension marker at a first end and abutting the distal endcap at a second end; and a plurality of visual marker bands wrapping around a cylindrical body of the tubular housing, each of the plurality of visual marker bands identifying a respective tension range, a position of the stopper disc tension marker relative to one or more of the plurality of visual marker bands providing a visual tension indication through the transparent sidewall portion of the tubular housing;

coupling a first portion of a first suture to the suture-engagement hook of the tension guide device outside of the housing of the tension guide device, the first portion of the first suture extending externally from a target organ, the first suture having a second portion deployed onto the target organ tissue within the target organ;

manually moving the housing of the tension guide device to cause compression of the spring of the tension guide device to increase a tension of the first suture by distally advancing the stopper disc tension marker toward the distal endcap of the housing; and determining whether the tension is within a target range using the tension guide device.

2. The method of claim 1, further comprising applying a label to the first portion or another portion of the first suture extending externally from the target organ.

3. The method of claim 2, wherein applying the label comprises coloring the first portion or the other portion of the first suture to provide a visual identifier that distinguishes the first suture from a second suture anchored to the target organ.

4. The method of claim 3, wherein coloring comprises running the first portion or the other portion of the first suture through a groove of a coloring applicator tip portion.

5. The method of claim 1, further comprising coupling a suture tab to the first portion or another portion of the first suture extending externally from the target organ to provide a visual identifier that distinguishes the first suture from a second suture anchored to the target organ.

6. The method of claim 5, wherein coupling the suture tab comprises winding the first portion or the other portion of the first suture around a neck portion of the suture tab defined by a pair of notches on opposite sides of the suture tab that separate a proximal manual grip lobe from a distal lobe that is smaller than the proximal manual grip lobe.

7. The method of claim 6, wherein coupling the first portion of the first suture to the tension guide device comprises engaging the tension guide device with the suture tab.

8. The method of claim 1, wherein coupling the first portion of the first suture to the tension guide device comprises wrapping the first suture around a base of a T-shaped form of the suture-engagement hook.

9. The method of claim 1, wherein determining whether the tension is within a target range comprises determining whether the stopper disc tension marker is within a target range indicated by one or more of the plurality of visual marker bands.

10. The method of claim 1, further comprising deploying a second suture onto a second site of the target organ tissue, selection of the second site being based at least in part on a response of the target organ tissue to the tension of the first suture.

11. The method of claim 1, wherein the target organ is a heart.

12. The method of claim 11, wherein the target organ tissue is a mitral valve leaflet.

* * * * *